United States Patent
Sakakibara et al.

(10) Patent No.: US 9,145,563 B2
(45) Date of Patent: Sep. 29, 2015

(54) TRANSGENIC PLANT HAVING INCREASED BIOMASS AND IMPROVED ENVIRONMENTAL STRESS RESISTANCE, AND PROCESS FOR PRODUCTION THEREOF

(75) Inventors: Hitoshi Sakakibara, Kanagawa (JP); Norihito Nakamichi, Kanagawa (JP); Nobue Makita, Kanagawa (JP)

(73) Assignee: RIKEN, Saitama (JP)

( * ) Notice: Subject to any disclaimer, the term of this patent is extended or adjusted under 35 U.S.C. 154(b) by 465 days.

(21) Appl. No.: 13/503,655

(22) PCT Filed: Oct. 22, 2010

(86) PCT No.: PCT/JP2010/069229
§ 371 (c)(1),
(2), (4) Date: Apr. 23, 2012

(87) PCT Pub. No.: WO2011/049243
PCT Pub. Date: Apr. 28, 2011

(65) Prior Publication Data
US 2012/0278948 A1 Nov. 1, 2012

Related U.S. Application Data

(60) Provisional application No. 61/291,300, filed on Dec. 30, 2009.

(30) Foreign Application Priority Data

Oct. 23, 2009 (JP) ................. 2009-244595

(51) Int. Cl.
*C12N 15/62* (2006.01)
*C07K 14/035* (2006.01)
*C07K 14/415* (2006.01)
*C12N 15/82* (2006.01)

(52) U.S. Cl.
CPC .......... *C12N 15/8261* (2013.01); *C07K 14/415* (2013.01); *C12N 15/8271* (2013.01); *C12N 15/8273* (2013.01)

(58) Field of Classification Search
USPC ........................................................ 800/290
See application file for complete search history.

(56) References Cited

FOREIGN PATENT DOCUMENTS

WO   WO 03/025184   *   3/2003

OTHER PUBLICATIONS

Sequence published as GenBank Accession No. BT005816 submitted Mar. 18, 2003; accessed Apr. 18, 2014.*
Sequence published as UniProtKB Accession No. Q9LKL2 submitted Sep. 27, 2004; accessed Apr. 18, 2014.*
Fujimori et al. (PRR5 (Pseudo-Response Regulator 5) Plays antagonistic roles to CCA1 (Circadian Clock-Associated 1) in *Arabidopsis thaliana*, 69 Biosci. Biotechnol. Biochem. No. 2, 426-430 (2005)).*
Parcy et al. (Interaction of Leafy, Agamous and Terminal FLOWER1 in maintaining floral meristem identity in *Arabidopsis*, 129 Decelopment, 2519-2527 (2002)).*
Zhang (Overexpression analysis of plant transcription factors, 6 Curr Op Plant Bio, 430-440 (2003)).*
UniProtKB Accession No. Q6LA42; published Sep. 27, 2004.*
GenBank Accession No. AY062114; published Nov. 24, 2001.*
Makino, S., et al., "The APRR1/TOC1 Quintet Implicated in Circadian Rhythms of *Arabidopsis thaliana*: I. Characterization with APRR1-Overexpressing Plants," Plant Cell Physiol., vol. 43, No. 1, pp. 58-69, (2002).
Matsushika, A., et al., "Characterization of Circadian-Associated Pseudo-Response Regulators: I. Comparative Studies on a Series of Transgenic Lines Misexpressing Five Distinctive PRR Genes in *Arabidopsis thaliana*," Biosci. Biotechnol. Biochem., vol. 71, No. 2, pp. 527-534, (2007).
Fujimori, T., et al., "PRR5 (Pseudo-Response Pregulator 5) Plays Antagonistic Roles to CCA1 (Circadian Clock-Associated 1) in *Arabidopsis thaliana*," Biosci. Biotechnol. Biochem., vol. 69, No. 2, pp. 426-430, (2005).
Makino, S., et al., "Genes Encoding Pseudo-Response Regulators: Insight into His-to-Asp Phosphorelay and Circadian Rhythm in *Arabidopsis thaliana*," Plant Cell Physiol., vol. 41, No. 6, pp. 791-803, (2000).
Mizuno, T., "Molecular basis for plant circadian clock and flowering: How does the quintet tell the time?" Protein, Nucleic Acid and Enzyme, vol. 47, No. 11, pp. 1421-1428, (2002).
Sakai, H., et al., "*Arabidopsis* ARR1 and ARR2 response regulators operate as transcriptional activators," The Plant Journal, vol. 24, No. 6, pp. 703-711, (2000).
Nakamichi, N., et al., "Shiroinunazuna no Giji Response Regulator wa Seibutsudokei de Kino suru Tensha Yokusei Inshi de aru," Proceedings from the 51st Annual Meeting of the Japanese Society of Plant Physiologists, p. 170, (Mar. 12, 2010).

* cited by examiner

*Primary Examiner* — Ashwin Mehta
*Assistant Examiner* — Stephen Uyeno
(74) *Attorney, Agent, or Firm* — Birch Stewart Kolasch & Birch, LLP

(57) ABSTRACT

An object of the present invention is to provide a transgenic plant on which a useful phenotype is conferred by regulating expression of pseudo-response regulator (PRR) genes with an approach that is different from deletion of PRR genes. According to the present invention, there is provided a transgenic plant into which a polynucleotide encoding a protein comprising a CCT motif and a pseudo-receiver domain which is a common motif of plant pseudo-response regulator genes, a fusion polynucleotide of said polynucleotide and a polynucleotide encoding at least one transcription activation domain of a transcription factor, or a recombinant vector comprising said polynucleotide or fusion polynucleotide has been introduced.

1 Claim, 12 Drawing Sheets
(7 of 12 Drawing Sheet(s) Filed in Color)

PRR1(TOC1), PRR3, PRR5, PRR7, PRR9

* t-test P<0.05, vs Vector control

TRANSGENIC PLANT HAVING INCREASED BIOMASS AND IMPROVED ENVIRONMENTAL STRESS RESISTANCE, AND PROCESS FOR PRODUCTION THEREOF

This application is the National Stage under 35 USC §371 of International Application Number PCT/JP2010/069229 filed on Oct. 22, 2010, which claims priority under 35 USC §119(a)-(d) of Application Number 2009-244595 filed on Oct. 23, 2009 in Japan, and priority under 35 USC §119(e) of Provisional Application No. 61/291,300 filed on Dec. 30, 2009 in the United States. The contents of JP2009-244595 and 61/291,300 are hereby incorporated by reference.

TECHNICAL FIELD

The present invention relates to a transgenic plant exhibiting increased biomass per plant individual and improved environmental stress resistance, and a method for preparing the same.

BACKGROUND ART

It has been suggested that the circadian clock system in *Arabidopsis thaliana* is associated with increased biomass, determination of the time of flowering, and environmental stress responses (Non-Patent Document 1). As a result of research conducted using *Arabidopsis thaliana*, three plant clock-associated genes (i.e., the circadian clock-associated 1 (CCA1) gene, the late elongated hypocotyl (LHY) gene, and the timing of cab expression 1 (TOC1) gene) have been discovered, and the mechanisms of plant circadian rhythm have been proved to be based on the transcriptional feedback loop of such a plurality of genes. Among these, the TOC1 gene is one of pseudo-response regulator genes. At present, a total of 5 genes (i.e., PRR3, PRR5, PRR7, and PRR9, in addition to TOC1 (PRR1)) have been identified as pseudo-response regulator genes in *Arabidopsis thaliana*, and the expression levels thereof increase and decrease in the order of PRR9, PRR7, PRR5, PRR3, and PRR1 (TOC1) from dawn toward evening in a phase-graded manner.

The present inventors had focused on and studied the prr9 prr7 prr5 triple mutant of *Arabidopsis thaliana* (i.e., the d975 mutant). As a result of previous studies, the d975 mutant was found to exhibit industrially useful phenotypes such as flowering stem elongation (Non-Patent Document 3), delayed flowering (Non-Patent Document 2), and higher resistance against low temperature or dehydration (Non-Patent Document 4), in addition to a breakdown of the circadian clock system (Non-Patent Document 2). However, since the three PRR genes complement their functions each other, a single mutant would not exhibit a remarkable phenotype (Non-Patent Document 2). In addition, conferring of a useful phenotype by deletion of the three PRR genes as targets would be attended with the difficulty in preparation of a multiple mutant. Further, since the biochemical functions of PRR9, PRR7, and PRR5 proteins are unknown, suppression of the functions of the PRR proteins with the use of a low-molecular-weight compound or the like is not practical technically.

An example of a technique for conferring low temperature resistance or dehydration resistance is a method in which expression of the DREB1A gene or similar genes is induced under the control of a dehydration stress responsive promoter of *Arabidopsis thaliana* (Patent Document 1 and Non-Patent Document 5). While this method may be sufficient to confer stress resistance, increased biomass is not mentioned.

Increased biomass is observed for a mutant of the clock-associated gene, GIGANTEA (gi) (Non-Patent Document 6); however, this mutant is more susceptible to low temperature stress (Non-Patent Document 7). Thus, a plant exhibiting increased biomass and environmental stress resistance cannot be prepared by a method of deleting the function of this gene as a target.

Slightly decreased expression levels of the clock-associated genes (i.e., the circadian clock associated 1 (CCA1) gene and the late elongated hypocotyl (LHY)) are said to be correlated with the increased biomass (Non-Patent Document 8); however, a line in which expression of the CCA1 gene and the LHY gene was completely suppressed (i.e., the ccal lhy double mutant) rather exhibits a decreased biomass (Non-Patent Document 9). Thus, it is considered difficult to increase the biomass by targeting these genes.

While the biological clocks of long-day plants are almost the same as those of short-day plants (Non-Patent Document 10), seasonal responses utilizing such biological clocks are known to differ from each other (Non-Patent Document 11). Accordingly, the degree of effectiveness of conferring a useful phenotype on a short-day plant by modifying a clock gene of a long-day plant (i.e., *Arabidopsis thaliana*) is unknown.

(Patent Document 1) JP Patent Publication (Kokai) No. 2000-116260 A
(Non-Patent Document 1) Harmer, S. L., Hogenesch, J. B., Straume, M., Chang, H. S., Han, B., Zhu, T., Wang, X., Kreps, J. A., and Kay, S. A., 2000, Orchestrated transcription of key pathways in *Arabidopsis* by the circadian clock, Science 290 (5499): 2110-2113
(Non-Patent Document 2) Nakamichi, N., Kita, M., Ito, S., Yamashino, T., and Mizuno, T., 2005, Pseudo-response regulators, PRR9, PRR7 and PRR5, together play essential roles similar to the circadian clock of *Arabidopsis thaliana*, Plant Cell Physiol., 46 (5): 686-698
(Non-Patent Document 3) Yamashino, T., Ito, S., Niwa, Y., Kunihiro, A., Nakamichi, N., and Mizuno, T., 2008, Involvement of *Arabidopsis* clock-associated pseudo-response regulators in diurnal oscillations of gene expression in the presence of environmental time cues, Plant Cell Physiol., 49 (12): 1839-1850
(Non-Patent Document 4) Nakamichi, N., Kusano, M., Fukushima, A., Kita, M., Ito, S., Yamashino, T., Saito, K., Sakakibara, H., and Mizuno, T., 2009, Transcript profiling of an *Arabidopsis* pseudo-response regulator arrhythmic triple mutant reveals a role for the circadian clock in cold stress response, Plant Cell Physiol., 50 (3): 447-462
(Non-Patent Document 5) Kasuga, M., Liu, Q., Miura, S., Yamaguchi-Shinozaki, K., and Shinozaki, K., 1999, Improving plant drought, salt, and freezing resistance by gene transfer of a single stress-inducible transcription factor, Nat. Biotechnol., 17 (3): 287-291
(Non-Patent Document 6) Redei, G., 1960, Supervital mutants of *Arabidopsis*, Genetics 47: 443-460
(Non-Patent Document 7) Cao, S., Ye, M., and Jiang, S., 2005, Involvement of GIGANTEA gene in the regulation of cold stress response in *Arabidopsis*, Plant Cell Rep., 24 (11): 683-690
(Non-Patent Document 8) Ni, Z., Kim, E. D., Ha, M., Lackey, E., Liu, J., Zhang, Y., Sun, Q., and Chen, Z. J., 2009, Altered circadian rhythms regulate growth vigour in hybrids and allopolyploids, Nature 457 (7227): 327-331
(Non-Patent Document 9) Mizoguchi, T., Wheatley, K., Hanzawa, Y., Wright, L., Mizoguchi, M., Song, H. R., Carre, I. A., and Coupland, G., 2002, LHY and CCA1 are partially redundant genes required to maintain circadian rhythms in *Arabidopsis*, Dev Cell 2 (5): 629-641

(Non-Patent Document 10) Murakami, M., Tago, Y., Yamashino, T., and Mizuno, T., 2007, Comparative overviews of clock-associated genes of *Arabidopsis thaliana* and *Oryza sativa, Plant Cell Physiol.*, 48 (1): 110-121

(Non-Patent Document 11) Hayama, R., Yokoi, S., Tamaki, S., Yano, M., and Shimamoto, K., 2003, Adaptation of photoperiodic control pathways produces short-day flowering in rice, Nature, 422 (6933): 719-722

DISCLOSURE OF INVENTION

Accordingly, it is an object of the present invention to provide a transgenic plant on which a useful phenotype is conferred by regulating functions of the pseudo-response regulator (PRR) genes with an approach that is different from deletion of the PRR genes.

The present inventors have conducted concentrated studies in order to attain the above object. As a result, they found that increased biomass and improved environmental stress resistance could be simultaneously achieved by forcibly expressing in a long-day plant, *Arabidopsis thaliana*, a fusion protein of a pseudo-response regulator (PRR), which is involved in a plant circadian clock system, and a transcription activation domain of a transcription factor. In addition, they found that increased biomass and improved environmental stress resistance could be achieved by forcibly expressing the pseudo-response regulator (PRR) alone in rice, which is a short-day plant. The present invention has been completed based on such findings.

Specifically, the present invention includes the following.

(1) A transgenic plant into which a fusion polynucleotide of a polynucleotide encoding a protein comprising a CCT motif and a pseudo-receiver domain which is a common motif of plant pseudo-response regulator genes and a polynucleotide encoding at least one transcription activation domain of a transcription factor, or a recombinant vector comprising the fusion polynucleotide has been introduced.

(2) The transgenic plant according to (1), wherein the polynucleotide encoding a protein comprising a CCT motif and a pseudo-receiver domain which is a common motif of plant pseudo-response regulator genes is any of polynucleotides (a) to (c) below:

(a) a polynucleotide consisting of the nucleotide sequence shown in SEQ ID NO: 1, 3, 5, 7 or 9;

(b) a polynucleotide that hybridizes under stringent conditions to a polynucleotide consisting of a nucleotide sequence complementary to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene; or (c) a polynucleotide that consists of a nucleotide sequence having 70% or higher homology to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene.

(3) The transgenic plant according to (1), wherein the polynucleotide encoding a protein comprising a CCT motif and a pseudo-receiver domain which is a common motif of plant pseudo-response regulator genes encodes any of proteins (d) to (f) below:

(d) a protein consisting of the amino acid sequence shown in SEQ ID NO: 2, 4, 6, 8 or 10;

(e) a protein consisting of an amino acid sequence derived from the amino acid sequence shown in SEQ ID NO: 2, 4, 6, 8 or 10 by deletion, substitution, or addition of one or several amino acids and having an activity of suppressing the transcription of the circadian clock-associated 1 (CCA1) gene or the late elongated hypocotyl (LHY) gene; or (f) a protein consisting of an amino acid sequence having 70% or higher homology to the amino acid sequence shown in SEQ ID NO: 2, 4, 6, 8 or 10 and having an activity of suppressing the transcription of the circadian clock-associated 1 (CCA1) gene or the late elongated hypocotyl (LHY) gene.

(4) The transgenic plant according to any of (1) to (3), wherein the polynucleotide encoding a transcription activation domain of a transcription factor is any of polynucleotides (g) to (i) below:

(g) a polynucleotide consisting of the nucleotide sequence shown in SEQ ID NO: 11;

(h) a polynucleotide that hybridizes under stringent conditions to a polynucleotide consisting of a nucleotide sequence complementary to the nucleotide sequence shown in SEQ ID NO: 11 and that encodes a protein having an activity of releasing the suppression of transcription of the circadian clock-associated 1 (CCA1) gene or the late elongated hypocotyl (LHY) gene upon fusion thereof to a PRR polynucleotide; or (i) a polynucleotide that consists of a nucleotide sequence having 70% or higher homology to the nucleotide sequence shown in SEQ ID NO: 11 and that encodes a protein having an activity of releasing the suppression of transcription of the circadian clock-associated 1 (CCA1) gene or the late elongated hypocotyl (LHY) gene upon fusion thereof to a PRR polynucleotide.

(5) The transgenic plant according to any of (1) to (4), which is a long-day plant.

(6) A transgenic plant into which a polynucleotide encoding a protein comprising a CCT motif and a pseudo-receiver domain which is a common motif of plant pseudo-response regulator genes, or a recombinant vector comprising the polynucleotide has been introduced.

(7) The transgenic plant according to (6), wherein the polynucleotide encoding a protein comprising a CCT motif and a pseudo-receiver domain which is a common motif of plant pseudo-response regulator genes is any of polynucleotides (a) to (c) below:

(a) a polynucleotide consisting of the nucleotide sequence shown in SEQ ID NO: 1, 3, 5, 7 or 9;

(b) a polynucleotide that hybridizes under stringent conditions to a polynucleotide consisting of a nucleotide sequence complementary to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene; or (c) a polynucleotide that consists of a nucleotide sequence having 70% or higher homology to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene.

(8) The transgenic plant according to (6), wherein the polynucleotide encoding a protein comprising a CCT motif and a pseudo-receiver domain which is a common motif of plant pseudo-response regulator genes encodes any of proteins (d) to (f) below:

(d) a protein consisting of the amino acid sequence shown in SEQ ID NO: 2, 4, 6, 8 or 10;

(e) a protein consisting of an amino acid sequence derived from the amino acid sequence shown in SEQ ID NO: 2, 4, 6, 8 or 10 by deletion, substitution, or addition of one or several amino acids and having an activity of suppressing the transcription of the circadian clock-associated 1 (CCA1) gene or the late elongated hypocotyl (LHY) gene; or (f) a protein consisting of an amino acid sequence having 70% or higher homology to the amino acid sequence shown in SEQ ID NO: 2, 4, 6, 8 or 10 and having an activity of suppressing the transcription of the circadian clock-associated 1 (CCA1) gene or the late elongated hypocotyl (LHY) gene.

(9) The transgenic plant according to any of (6) to (8), which is a short-day plant.

(10) The transgenic plant according to any of (1) to (9), which exhibits increased biomass.

(11) The transgenic plant according to any of (1) to (9), on which environmental stress resistance is conferred.

(12) The transgenic plant according to (11), wherein the environmental stress is at least one form of stress selected from the group consisting of dehydration stress, low temperature stress, and salt stress.

(13) A method for preparing a transgenic plant, comprising:

introducing a fusion polynucleotide of a polynucleotide encoding a protein comprising a CCT motif and a pseudo-receiver domain which is a common motif of plant pseudo-response regulator genes and a polynucleotide encoding at least one transcription activation domain of a transcription factor, or a recombinant vector comprising the fusion polynucleotide into a plant cell; and regenerating a plant body from the plant cell.

(14) The method according to (13), wherein the polynucleotide encoding a protein comprising a CCT motif and a pseudo-receiver domain which is a common motif of plant pseudo-response regulator genes is any of polynucleotides (a) to (c) below:

(a) a polynucleotide consisting of the nucleotide sequence shown in SEQ ID NO: 1, 3, 5, 7 or 9;

(b) a polynucleotide that hybridizes under stringent conditions to a polynucleotide consisting of a nucleotide sequence complementary to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene; or (c) a polynucleotide that consists of a nucleotide sequence having 70% or higher homology to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene.

(15) The method according to (13), wherein the polynucleotide encoding a protein comprising a CCT motif and a pseudo-receiver domain which is a common motif of plant pseudo-response regulator genes encodes any of proteins (d) to (f) below:

(d) a protein consisting of the amino acid sequence shown in SEQ ID NO: 2, 4, 6, 8 or 10;

(e) a protein consisting of an amino acid sequence derived from the amino acid sequence shown in SEQ ID NO: 2, 4, 6, 8 or 10 by deletion, substitution, or addition of one or several amino acids and having an activity of suppressing the transcription of the circadian clock-associated 1 (CCA1) gene or the late elongated hypocotyl (LHY) gene; or (f) a protein consisting of an amino acid sequence having 70% or higher homology to the amino acid sequence shown in SEQ ID NO: 2, 4, 6, 8 or 10 and having an activity of suppressing the transcription of the circadian clock-associated 1 (CCA1) gene or the late elongated hypocotyl (LHY) gene.

(16) The method according to any of (13) to (15), wherein the polynucleotide encoding a transcription activation domain of a transcription factor is any of polynucleotides (g) to (i) below:

(g) a polynucleotide consisting of the nucleotide sequence shown in SEQ ID NO: 11;

(h) a polynucleotide that hybridizes under stringent conditions to a polynucleotide consisting of a nucleotide sequence complementary to the nucleotide sequence shown in SEQ ID NO: 11 and that encodes a protein having an activity of releasing the suppression of transcription of the circadian clock-associated 1 (CCA1) gene or the late elongated hypocotyl (LHY) gene upon fusion thereof to a PRR polynucleotide; or (i) a polynucleotide that consists of a nucleotide sequence having 70% or higher homology to the nucleotide sequence shown in SEQ ID NO: 11 and that encodes a protein having an activity of releasing the suppression of transcription of the circadian clock-associated 1 (CCA1) gene or the late elongated hypocotyl (LHY) gene upon fusion thereof to a PRR polynucleotide.

(17) The method according to any of (13) to (16), wherein the plant is a long-day plant.

(18) A method for preparing a transgenic plant, comprising:

introducing a polynucleotide encoding a protein comprising a CCT motif and a pseudo-receiver domain which is a common motif of plant pseudo-response regulator genes, or a recombinant vector comprising the polynucleotide into a plant cell; and regenerating a plant body from the plant cell.

(19) The method according to (18), wherein the polynucleotide encoding a protein comprising a CCT motif and a pseudo-receiver domain which is a common motif of plant pseudo-response regulator genes is any of polynucleotides (a) to (c) below:

(a) a polynucleotide consisting of the nucleotide sequence shown in SEQ ID NO: 1, 3, 5, 7 or 9;

(b) a polynucleotide that hybridizes under stringent conditions to a polynucleotide consisting of a nucleotide sequence complementary to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene; or (c) a polynucleotide that consists of a nucleotide sequence having 70% or higher homology to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene.

(20) The method according to (18), wherein the polynucleotide encoding a protein comprising a CCT motif and a pseudo-receiver domain which is a common motif of plant pseudo-response regulator genes encodes any of proteins (d) to (f) below:

(d) a protein consisting of the amino acid sequence shown in SEQ ID NO: 2, 4, 6, 8 or 10;

(e) a protein consisting of an amino acid sequence derived from the amino acid sequence shown in SEQ ID NO: 2, 4, 6, 8 or 10 by deletion, substitution, or addition of one or several amino acids and having an activity of suppressing the transcription of the circadian clock-associated 1 (CCA1) gene or the late elongated hypocotyl (LHY) gene; or (f) a protein consisting of an amino acid sequence having 70% or higher homology to the amino acid sequence shown in SEQ ID NO: 2, 4, 6, 8 or 10 and having an activity of suppressing the transcription of the circadian clock-associated 1 (CCA1) gene or the late elongated hypocotyl (LHY) gene.

(21) The method according to any of (18) to (20), wherein the plant is a short-day plant.

(22) The method according to any of (13) to (21), wherein the transgenic plant exhibits increased biomass.

(23) The method according to any of (13) to (21), wherein the transgenic plant has environmental stress resistance.

(24) The method according to (23), wherein the environmental stress is at least one form of stress selected from the group consisting of dehydration stress, low temperature stress, and salt stress.

(25) A method for increasing the biomass of a plant, comprising overexpressing in a plant a fusion polynucleotide of a polynucleotide encoding a protein comprising a CCT motif and a pseudo-receiver domain which is a common motif of plant pseudo-response regulator genes and a polynucleotide encoding at least one transcription activation domain of a transcription factor.

(26) The method according to (25), wherein the polynucleotide encoding a protein comprising a CCT motif and a pseudo-receiver domain which is a common motif of plant pseudo-response regulator genes is any of polynucleotides (a) to (c) below:

(a) a polynucleotide consisting of the nucleotide sequence shown in SEQ ID NO: 1, 3, 5, 7 or 9;

(b) a polynucleotide that hybridizes under stringent conditions to a polynucleotide consisting of a nucleotide sequence complementary to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene; or (c) a polynucleotide that consists of a nucleotide sequence having 70% or higher homology to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene.

(27) The method according to (25), wherein the polynucleotide encoding a protein comprising a CCT motif and a pseudo-receiver domain which is a common motif of plant pseudo-response regulator genes encodes any of proteins (d) to (f) below:

(d) a protein consisting of the amino acid sequence shown in SEQ ID NO: 2, 4, 6, 8 or 10;

(e) a protein consisting of an amino acid sequence derived from the amino acid sequence shown in SEQ ID NO: 2, 4, 6, 8 or 10 by deletion, substitution, or addition of one or several amino acids and having an activity of suppressing the transcription of the circadian clock-associated 1 (CCA1) gene or the late elongated hypocotyl (LHY) gene; or (f) a protein consisting of an amino acid sequence having 70% or higher homology to the amino acid sequence shown in SEQ ID NO: 2, 4, 6, 8 or 10 and having an activity of suppressing the transcription of the circadian clock-associated 1 (CCA1) gene or the late elongated hypocotyl (LHY) gene.

(28) The method according to any of (25) to (27), wherein the polynucleotide encoding a transcription activation domain of a transcription factor is any of polynucleotides (g) to (i) below:

(g) a polynucleotide consisting of the nucleotide sequence shown in SEQ ID NO: 11;

(h) a polynucleotide that hybridizes under stringent conditions to a polynucleotide consisting of a nucleotide sequence complementary to the nucleotide sequence shown in SEQ ID NO: 11 and that encodes a protein having an activity of releasing the suppression of transcription of the circadian clock-associated 1 (CCA1) gene or the late elongated hypocotyl (LHY) gene via fusion thereof to the PRR polynucleotide; or (i) a polynucleotide that consists of a nucleotide sequence having 70% or higher homology to the nucleotide sequence shown in SEQ ID NO: 11 and that encodes a protein having an activity of releasing the suppression of transcription of the circadian clock-associated 1 (CCA1) gene or the late elongated hypocotyl (LHY) gene upon fusion thereof to a PRR polynucleotide.

(29) The method according to any of (25) to (28), wherein the plant is a long-day plant.

(30) A method for increasing the biomass of a plant, comprising overexpressing in a plant a polynucleotide encoding a protein comprising a CCT motif and a pseudo-receiver domain which is a common motif of plant pseudo-response regulator genes.

(31) The method according to (30), wherein the polynucleotide encoding a protein comprising a CCT motif and a pseudo-receiver domain which is a common motif of plant pseudo-response regulator genes is any of polynucleotides (a) to (c) below:

(a) a polynucleotide consisting of the nucleotide sequence shown in SEQ ID NO: 1, 3, 5, 7 or 9;

(b) a polynucleotide that hybridizes under stringent conditions to a polynucleotide consisting of a nucleotide sequence complementary to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene; or (c) a polynucleotide that consists of a nucleotide sequence having 70% or higher homology to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene.

(32) The method according to (30), wherein the polynucleotide encoding a protein comprising a CCT motif and a pseudo-receiver domain which is a common motif of plant pseudo-response regulator genes encodes any of proteins (d) to (f) below:

(d) a protein consisting of the amino acid sequence shown in SEQ ID NO: 2, 4, 6, 8 or 10;

(e) a protein consisting of an amino acid sequence derived from the amino acid sequence shown in SEQ ID NO: 2, 4, 6, 8 or 10 by deletion, substitution, or addition of one or several amino acids and having an activity of suppressing the transcription of the circadian clock-associated 1 (CCA1) gene or the late elongated hypocotyl (LHY) gene; or (f) a protein consisting of an amino acid sequence having 70% or higher homology to the amino acid sequence shown in SEQ ID NO: 2, 4, 6, 8 or 10 and having an activity of suppressing the transcription of the circadian clock-associated 1 (CCA1) gene or the late elongated hypocotyl (LHY) gene.

(33) The method according to any of (30) to (32), wherein the plant is a short-day plant.

(34) A method for conferring environmental stress resistance on a plant, comprising overexpressing in a plant a fusion polynucleotide of a polynucleotide encoding a protein comprising a CCT motif and a pseudo-receiver domain which is a common motif of plant pseudo-response regulator genes and a polynucleotide encoding at least one transcription activation domain of a transcription factor.

(35) The method according to (34), wherein the polynucleotide encoding a protein comprising a CCT motif and a pseudo-receiver domain which is a common motif of plant pseudo-response regulator genes is any of polynucleotides (a) to (c) below:

(a) a polynucleotide consisting of the nucleotide sequence shown in SEQ ID NO: 1, 3, 5, 7 or 9;

(b) a polynucleotide that hybridizes under stringent conditions to a polynucleotide consisting of a nucleotide sequence complementary to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene; or (c) a polynucleotide that consists of a nucleotide sequence having 70% or higher homology to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene.

(36) The method according to (34), wherein the polynucleotide encoding a protein comprising a CCT motif and a pseudo-receiver domain which is a common motif of plant pseudo-response regulator genes encodes any of proteins (d) to (f) below:

(d) a protein consisting of the amino acid sequence shown in SEQ ID NO: 2, 4, 6, 8 or 10;

(e) a protein consisting of an amino acid sequence derived from the amino acid sequence shown in SEQ ID NO: 2, 4, 6, 8 or 10 by deletion, substitution, or addition of one or several amino acids and having an activity of suppressing the transcription of the circadian clock-associated 1 (CCA1) gene or the late elongated hypocotyl (LHY) gene; or (f) a protein consisting of an amino acid sequence having 70% or higher homology to the amino acid sequence shown in SEQ ID NO: 2, 4, 6, 8 or 10 and having an activity of suppressing the transcription of the circadian clock-associated 1 (CCA1) gene or the late elongated hypocotyl (LHY) gene.

(37) The method according to any of (34) to (36), wherein the polynucleotide encoding a transcription activation domain of a transcription factor is any of polynucleotides (g) to (i) below:

(g) a polynucleotide consisting of the nucleotide sequence shown in SEQ ID NO: 11;

(h) a polynucleotide that hybridizes under stringent conditions to a polynucleotide consisting of a nucleotide sequence complementary to the nucleotide sequence shown in SEQ ID NO: 11 and that encodes a protein having an activity of releasing the suppression of transcription of the circadian clock-associated 1 (CCA1) gene or the late elongated hypocotyl (LHY) gene upon fusion thereof to a PRR polynucleotide; or (i) a polynucleotide that consists of a nucleotide sequence having 70% or higher homology to the nucleotide sequence shown in SEQ ID NO: 11 and that encodes a protein having an activity of releasing the suppression of transcription of the circadian clock-associated 1 (CCA1) gene or the late elongated hypocotyl (LHY) gene upon fusion thereof to a PRR polynucleotide.

(38) The method according to any of (34) to (37), wherein the plant is a long-day plant.

(39) A method for conferring environmental stress resistance on a plant, comprising overexpressing in a plant a polynucleotide encoding a protein comprising a CCT motif and a pseudo-receiver domain which is a common motif of plant pseudo-response regulator genes.

(40) The method according to (39), wherein the polynucleotide encoding a protein comprising a CCT motif and a pseudo-receiver domain which is a common motif of plant pseudo-response regulator genes is any of polynucleotides (a) to (c) below:

(a) a polynucleotide consisting of the nucleotide sequence shown in SEQ ID NO: 1, 3, 5, 7 or 9;

(b) a polynucleotide that hybridizes under stringent conditions to a polynucleotide consisting of a nucleotide sequence complementary to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene; or (c) a polynucleotide that consists of a nucleotide sequence having 70% or higher homology to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene.

(41) The method according to (39), wherein the polynucleotide encoding a protein comprising a CCT motif and a pseudo-receiver domain which is a common motif of plant pseudo-response regulator genes encodes any of proteins (d) to (f) below:

(d) a protein consisting of the amino acid sequence shown in SEQ ID NO: 2, 4, 6, 8 or 10;

(e) a protein consisting of an amino acid sequence derived from the amino acid sequence shown in SEQ ID NO: 2, 4, 6, 8 or 10 by deletion, substitution, or addition of one or several amino acids and having an activity of suppressing the transcription of the circadian clock-associated 1 (CCA1) gene or the late elongated hypocotyl (LHY) gene; or (f) a protein consisting of an amino acid sequence having 70% or higher homology to the amino acid sequence shown in SEQ ID NO: 2, 4, 6, 8 or 10 and having an activity of suppressing the transcription of the circadian clock-associated 1 (CCA1) gene or the late elongated hypocotyl (LHY) gene.

(42) The method according to any of (39) to (41), wherein the plant is a short-day plant.

(43) The method according to any of (34) to (42), wherein the environmental stress is at least one form of stress selected from the group consisting of dehydration stress, low temperature stress, and salt stress.

BRIEF DESCRIPTION OF DRAWINGS

The file of this patent contains at least one drawing/photograph executed in color. Copies of this patent with color drawings/photographs will be provided by the Office upon request and payment of the necessary fee.

BEST MODES FOR CARRYING OUT THE INVENTION

Hereinafter, the present invention is described in detail.
1. Polynucleotide

A polynucleotide used for preparing the transgenic plant of the present invention is a polynucleotide encoding a protein comprising a CCT motif and a pseudo-receiver domain which is a common motif of plant pseudo-response regulator genes or a fusion polynucleotide of said polynucleotide and a polynucleotide encoding at least one transcription activation domain of a transcription factor.

Figure 1:
FIG. 1 shows the common structure of the PRR1 (TOC1), PRR3, PRR5, PRR7, and PRR9 genes, which are pseudo-response regulator genes.

Examples of the polynucleotide encoding a protein comprising a CCT motif and a pseudo-receiver domain include the PRR1 (TOC1), PRR3, PRR5, PRR7 and PRR9 genes, which are pseudo-response regulator genes. The PRR1 (TOC1), PRR3, PRR5, PRR7 and PRR9 genes have a common structure as shown in FIG. 1.

SEQ ID NOs: 1, 3, 5, 7 and 9 show the nucleotide sequences of the PRR1 (TOC1), PRR3, PRR5, PRR7 and PRR9 genes, and SEQ ID NOs: 2, 4, 6, 8 and 10 show the amino acid sequences encoded by said nucleotide sequences.

The pseudo-receiver domain is a motif that is found in common in pseudo-response regulator genes, and it is known to have an ability of protein-protein interaction. SEQ ID NOs: 12, 13, 14, 15 and 16 show the amino acid sequences of the pseudo-receiver domains of the PRR1 (TOC1), PRR3, PRR5, PRR7 and PRR9 genes.

Further, the CCT motif is a structure that is often observed in plant proteins, is rich in basic amino acids, and is composed of about 45 amino acids. The CCT motif of the CONSTANS (CO) protein of *Arabidopsis thaliana* is known to be involved in nuclear localization and protein-protein interaction. SEQ ID NOs: 17, 18, 19, 20 and 21 show the amino acid sequences of the CCT motifs of the PRR1 (TOC1), PRR3, PRR5, PRR7 and PRR9 genes.

Polynucleotides encoding proteins comprising a CCT motif and a pseudo-receiver domain (hereinafter referred to as "PRR polynucleotides") are considered to be widely distributed in the plant kingdom. Examples thereof include, but are not limited to, rice (Gramineae), poplar (Salicaceae), grape (Vitaceae), tomato (Solanaceae), cassava (Euphorbiaceae), soybean (Leguminosae), gymnosperms, ferns, and mosses, in addition to *Arabidopsis thaliana* (Brassicaceae).

In the present invention, a polynucleotide consisting of a nucleotide sequence similar to the nucleotide sequence shown in SEQ ID NO: 1, 3, 5, 7 or 9 can be used as a PRR polynucleotide like a polynucleotide consisting of the nucleotide sequence shown in SEQ ID NO: 1, 3, 5, 7 or 9, provided that it has a function equivalent to that of the polynucleotide consisting of the nucleotide sequence shown in SEQ ID NO: 1, 3, 5, 7 or 9. Accordingly, a polynucleotide consisting of a nucleotide sequence similar to the nucleotide sequence shown in the above sequence identification number and encoding a protein having an activity of suppressing the transcription of the circadian clock-associated 1 (CCA1) gene or the late elongated hypocotyl (LHY) gene is encompassed by the PRR polynucleotide used in the present invention. Such a polynucleotide may be naturally occurring or artificially prepared. For example, a homolog of the nucleotide sequence shown in the above sequence identification number (including an ortholog and a paralog) or a sequence having an artificially introduced mutation may be used.

Specific examples include the polynucleotides shown below:

(i) a polynucleotide that hybridizes under stringent conditions to a polynucleotide consisting of a nucleotide sequence complementary to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene;

(ii) a polynucleotide that consists of a nucleotide sequence having 70% or higher homology to the nucleotide sequence shown in SEQ ID NO: 1, 3, 5, 7 or 9 and that encodes a protein having an activity of suppressing the transcription of the circadian clock-associated 1 (CCA1) gene or the late elongated hypocotyl (LHY) gene;

(iii) a polynucleotide encoding a protein consisting of the amino acid sequence shown in SEQ ID NO: 2, 4, 6, 8 or 10;

(iv) a polynucleotide consisting of an amino acid sequence derived from the amino acid sequence shown in SEQ ID NO: 2, 4, 6, 8 or 10 by deletion, substitution, or addition of one or several amino acids and encoding a protein having an activity of suppressing the transcription of the circadian clock-associated 1 (CCA1) gene or the late elongated hypocotyl (LHY) gene; and (v) a polynucleotide consisting of an amino acid sequence having 70% or higher homology to the amino acid sequence shown in SEQ ID NO: 2, 4, 6, 8 or 10 and encoding a protein having an activity of suppressing the transcription of the circadian clock-associated 1 (CCA1) gene or the late elongated hypocotyl (LHY) gene.

The "circadian clock-associated 1 (CCA1) gene" is a morning gene that constitutes the circadian clock system and exhibits the maximum expression level in the morning. The term "activity of suppressing the transcription of the CCA1 gene" refers to an activity of suppressing the transcription of said gene and decreasing the expression level thereof. The "late elongated hypocotyl (LHY) gene" is a gene functionally homologous to the CCA1 gene.

The term "stringent conditions" as used herein refers to the conditions under which so-called specific hybrids are formed but non-specific hybrids are not formed. A person skilled in the art can adequately select the stringent hybridization conditions by referring to Sambrook et al., Molecular Cloning, A Laboratory Manual, 3rd Ed., Cold Spring Harbor Laboratory, 2001. For example, hybridization is carried out by performing pre-hybridization in a hybridization solution containing 25% formamide, or 50% formamide for more stringent conditions, 4×SSC, 50 mM HEPES (pH 7.0), 10× Denhart's solution, and 20 μg/ml denatured salmon sperm DNA at 42° C. overnight, adding a labeled probe thereto, and incubating the resultant at 42° C. overnight. In the subsequent step of washing, the washing solution and temperature conditions are approximately "1×SSC, 0.1% SDS, 37° C.," approximately "0.5× SSC, 0.1% SDS, 42° C." for more stringent conditions, and approximately "0.2×SSC, 0.1% SDS, 65° C." for even more stringent conditions. The degree of stringency is increased as the temperature becomes higher and the salt concentration becomes lower. This enables isolation of more homologous polynucleotides.

It should be noted that the combinations of SSC, SDS and temperature conditions described above are examples. A person skilled in the art can adequately combine the above or other factors that determine the hybridization stringency (e.g., probe concentration, probe length, and hybridization duration) to realize stringency similar to that described above.

A polynucleotide obtained via hybridization carried out under the above stringent conditions usually has high homology to DNA represented by the nucleotide sequence shown in any of SEQ ID NOs: 1, 3, 5, 7 and 9. The term "high homology" as used herein refers to the sequence homology of 70% or higher, preferably 80% or higher, 85% or higher, more preferably 90% or higher, further preferably 95% or higher, and most preferably 97% or higher (e.g., 98% to 99%) to any of the nucleotide sequences shown in the above sequence identification numbers.

In relation to the expression "amino acid sequence derived by deletion, substitution, or addition of one or several amino acids", the number of amino acids that may be deleted, substituted or added is the number of amino acids that can be deleted, substituted or added in accordance with a known method for preparing mutant proteins, such as site-directed mutagenesis. The number is not limited as long as the aforementioned activity is maintained. Usually, the number is for example 1 to 20, preferably 1 to 10, and more preferably 1 to 5. The term "mutation" as used herein primarily means a mutation that is artificially introduced in accordance with a known method for preparing mutant proteins, although a naturally occurring similar mutation may be employed.

The term "70% or higher homology" used in relation to the amino acid sequence refers to sequence homology of preferably 80% or higher, 85% or higher, more preferably 90% or higher, further preferably 95% or higher, and most preferably 97% or higher (e.g., 98% to 99%). Identity of sequence (amino acid sequence, nucleotide sequence) can be determined using the FASTA search or the BLAST search.

The PRR polynucleotide used in the present invention can be prepared using a known technique. For example, total mRNA may be prepared from an *Arabidopsis thaliana* tissue extract, primers may be designed based on the nucleotide sequence shown in the above sequence identification number, and full-length cDNA of the nucleotide sequence shown in the above sequence identification number can be obtained by performing the RACE method or the like. Alternatively, a cDNA library may be prepared from an *Arabidopsis thaliana* tissue extract, a probe may be designed based on the nucleotide sequence shown in the above sequence identification number, and the PRR polynucleotide of interest can be obtained using the hybridization method. Further, the PRR polynucleotide may be artificially synthesized based on the nucleotide sequence shown in the above sequence identification number.

A person skilled in the art can readily obtain a homologue of the PRR polynucleotide by referring to, for example, Molecular Cloning (Sambrook, J. et al., Molecular Cloning: A Laboratory Manual 3rd ed., Cold Spring Harbor Laboratory Press, 10 Skyline Drive Plainview, N.Y., 2001).

For example, deletion, addition and substitution of an amino acid can be carried out by introducing a mutation into a gene encoding the above protein using a technique known in the art. Mutation can be introduced into a gene by a known technique such as the Kunkel method or the Gapped duplex method, or a method in accordance therewith. For example, a kit for introducing mutation that utilizes the site-directed mutagenesis method (e.g., Mutant-K (TAKARA) or Mutant-G (TAKARA)), or the kit of LA PCR in vitro Mutagenesis series (TAKARA)) can be used. Alternatively, a sequence having a mutation being introduced into the nucleotide sequence shown in the above sequence identification number may be synthesized using a commercially available nucleic acid synthesis apparatus.

On the other hand, a polynucleotide encoding at least one transcription activation domain of a transcription factor which is to be fused to the PRR polynucleotide has a function of releasing the suppression of transcription of the circadian clock-associated 1 (CCA1) gene or the late elongated hypocotyl (LHY) gene due to the PRR polynucleotide and activating the transcription. Any transcription activation domain of a transcription factor may be used as long as it has the ability to activate the transcription. Specific examples include a transcription activation domain of the herpesvirus VP16 protein and a transcription activation domain of the yeast GAL4 protein. At least one transcription activation domain may be used, or two or more transcription activation domains of the same type or different types may be used in combination. A polynucleotide encoding the transcription activation domain of the herpesvirus VP16 protein is shown in SEQ ID NO: 11. A polynucleotide consisting of a nucleotide sequence similar to the nucleotide sequence shown in SEQ ID NO: 11 may be used, provided that it has a function of releasing the suppression of transcription of the circadian clock-associated 1 (CCA1) gene or the late elongated hypocotyl (LHY) gene and activating the transcription upon fusion thereof to a PRR polynucleotide. Examples thereof include: a polynucleotide hybridizing under stringent conditions to a polynucleotide consisting of a nucleotide sequence complementary to the nucleotide sequence shown in SEQ ID NO: 11 and encoding a protein having an activity of releasing the suppression of transcription of the circadian clock-associated 1 (CCA1) gene or the late elongated hypocotyl (LHY) gene upon fusion thereof to a PRR polynucleotide; and a polynucleotide consisting of a nucleotide sequence having 70% or higher homology to the nucleotide sequence shown in SEQ ID NO: 11 and encoding a protein having an activity of releasing the suppression of transcription of the circadian clock-associated 1 (CCA1) gene or the late elongated hypocotyl (LHY) gene upon fusion thereof to a PRR polynucleotide. The meanings of "stringent" and "homology" are as defined above.

2. Recombinant Vector

The recombinant vector of the present invention used for plant transformation can be constructed by incorporating the above polynucleotide or fusion polynucleotide (hereinafter referred to as "target gene") into an adequate vector. Examples of vectors that can be preferably used include pBI, pPZP, pSMA, and pCAMBIA vectors which can introduce the target gene into a plant via *Agrobacterium*. Use of pBI binary vectors or intermediate vectors is particularly preferable, and examples thereof include pBI121, pBI101, pBI101.2, and pBI101.3. The term "binary vector" refers to a shuttle vector replicable in *Escherichia coli* and *Agrobacterium*. When a plant is infected with *Agrobacterium* that harbors a binary vector, DNA located in a region defined by the border sequences (LB sequence and RB sequence) on the vector can be integrated into plant nuclear DNA. On the other hand, pUC vectors are capable of directly introducing a gene into a plant, and examples thereof include pUC18, pUC19 and pUC9. Further, plant virus vectors, such as cauliflower mosaic virus (CaMV), bean golden mosaic virus (BGMV), and tobacco mosaic virus (TMV) vectors, can also be used.

When a binary vector plasmid is used, a target gene is inserted into a site between border sequences (LB and RB sequences) of the binary vector, and the recombinant vector is amplified in *Escherichia coli*. Subsequently, the amplified recombinant vector is introduced into, for example, *Agrobacterium tumefaciens* GV3101, C58, LBA4404, EHA101 or EHA105, or *Agrobacterium rhizogenes* LBA1334, by the electroporation method or the like, and the *Agrobacterium* is used for plant transduction.

In addition to the above-mentioned method, the three-member conjugation method (Nucleic Acids Research, 12: 8711, 1984) can be used to prepare *Agrobacterium* containing a target gene to be used for plant infection. Specifically, *Escherichia coli* harboring a plasmid comprising a target gene, *Escherichia coli* harboring a helper plasmid (e.g., pRK2013), and *Agrobacterium* are subjected to mixed culture on a medium containing rifampicin and kanamycin. Then, a conjugate *Agrobacterium* to be used for plant infection can be obtained.

For inserting a target gene into a vector, one may employ a method in which purified DNA is first cleaved with an adequate restriction enzyme and the cleaved fragment is then inserted into a restriction enzyme site or multicloning site of adequate vector DNA to connect the fragment to the vector.

In addition, it is necessary that a target gene be incorporated into a vector in such a manner that the gene is able to exert its functions. Thus, a promoter, an enhancer, a terminator, a replication origin that allows the use of a binary vector (e.g., a replication origin derived from Ti or Ri plasmid), a selection marker gene, and the like can be connected to a site upstream, inside, or downstream of the target gene in the vector.

A "promoter" may not be derived from a plant, provided that it is DNA that can function in a plant cell and bring about expression in a given tissue or at a given growth stage of a plant. Specific examples include cauliflower mosaic virus (CaMV) 35S promoter, nopaline synthase gene promoter (Pnos), maize-derived ubiquitin promoter, rice-derived actin promoter, and tobacco-derived PR protein promoter. When a target gene is to be expressed specifically in a given organ, a promoter that is expressed in a tissue-specific manner can be used. For example, the biomass-increasing effect of the polynucleotide of the present invention can be efficiently attained by using a flowering stem-specific gene or shoot apex-specific gene promoter.

An enhancer is used, for example, for increasing the expression efficiency of a target gene. Examples thereof include an enhancer region that comprises an upstream sequence in the CaMV 35S promoter.

Any sequence may be used as a terminator, provided that it can terminate transcription of a gene transcribed by a promoter. Examples thereof include terminators of the nopaline synthase (NOS) gene, the octopine synthase (OCS) gene, and the CaMV 35S RNA gene.

Examples of selection marker genes include ampicillin-resistant gene, neomycin-resistant gene, hygromycin-resistant gene, bialaphos-resistant gene, and dihydrofolate reductase gene.

The selection marker gene may be connected to a single plasmid together with a target gene as described above to prepare a recombinant vector. Alternatively, a recombinant vector obtained by connecting the selection marker gene to a plasmid and a recombinant vector obtained by connecting a target gene may be separately prepared. When the vectors are separately prepared, the vectors are co-transfected (co-introduced) into a host.

3. Transgenic Plant and Method for Preparing the Same

The transgenic plant of the present invention can be prepared by introducing a polynucleotide, a fusion polynucleotide, or a recombinant vector as described above (hereinafter collectively referred to as "target gene") into a target plant. In the present invention, the term "introduction of a gene" means that a target gene is introduced into cells of a host plant in a manner that allows the gene to express using, for example, a known genetic engineering technique. The introduced gene may be integrated into the genomic DNA of a host plant or may be present being comprised in a foreign vector.

As a method for introducing the target gene into a plant as described above, one of a variety of methods that have been reported and established can be adequately utilized. Examples thereof include the *Agrobacterium* method, the PEG-calcium phosphate method, the electroporation method, the liposome method, the particle gun method, and the microinjection method. When the *Agrobacterium* method is employed, a protoplast, a tissue section, or a plant body as it is (i.e., the in planta method) may be used. When a protoplast is used, the introduction can be carried out using a method in which the protoplast is co-cultured with *Agrobacterium* harboring a Ti plasmid or an Ri plasmid (for *Agrobacterium tumefaciens* or *Agrobacterium rhizogenes*, respectively), or the protoplast is fused to *Agrobacterium* which has been converted to a spheroplast (the spheroplast method). When a tissue section is used, the introduction can be carried out using a method in which an aseptically cultured leaf disc of a target plant is infected, or a callus (cultured undifferentiated cell) is infected. When the in planta method using a seed or a plant body is employed (i.e., in a system that does not involve tissue culture with the addition of plant hormones), the introduction can be carried out by direct treatment of an imbibed seed, a young seedling, a potted plant, or the like with *Agrobacterium*. These plant transformation methods can be carried out in accordance with the descriptions of general textbooks such as "Shinban, Model shokubutsu no jikken protocol, Idengakuteki shuhou kara genome kaiseki made (New edition, Experimental protocols for model plants, From genetic engineering technique to genome analysis), 2001, supervised by Isao Shimamoto & Kiyotaka Okada, Shujunsha."

One can confirm whether or not a target gene has been incorporated into a plant using the PCR method, the Southern hybridization method, the Northern hybridization method, the Western blotting method or the like. For example, DNA is prepared from a transgenic plant, primers specific for the target gene are designed, and PCR is then carried out. After PCR has been carried out, the amplification product is subjected to agarose gel electrophoresis, polyacrylamide gel electrophoresis, capillary electrophoresis or the like, and stained with ethidium bromide, a SYBR Green solution or the like. Transformation can be confirmed based on detection of the amplification product as a single band. Alternatively, the amplification product can be detected by carrying out PCR with the use of primers that have been labeled with a fluorescent dye or the like beforehand. Further, one may use a method in which the amplification product is bound to a solid phase such as a microplate, and confirmed using fluorescence, an enzymatic reaction or the like. Further, one may confirm that a target gene introduced into a plant cell is expressed (that is, the plant is transformed) by extracting proteins from the plant cell, fractionating the proteins by two-dimensional electrophoresis, and detecting a band of the protein encoded by the target gene.

Alternatively, a vector in which one of a variety of reporter genes (e.g., a gene for β-glucuronidase (GUS), luciferase (LUC), green fluorescent protein (GFP), chloramphenicol acetyltransferase (CAT) or β-galactosidase (LacZ)) is connected downstream of a target gene is prepared. *Agrobacterium* into which the aforementioned vector has been introduced is used to transform a plant in a manner similar to that as described above. Then, the expression of the reporter gene is measured. Thereby, transformation of the plant can be confirmed.

The plant used for transformation in the present invention may be a monocotyledonous plant or a dicotyledonous plant, or a short-day plant or a long-day plant. In case of a short-day plant (e.g., rice, maize, soybean, chrysanthemum, morning glory, or cosmos), transformation is carried out by introducing a polynucleotide encoding a protein comprising a CCT motif and a pseudo-receiver domain which is a common motif of plant pseudo-response regulator genes as described above. In case of a long-day plant (e.g., *Arabidopsis thaliana*, wheat, barley, spinach, or poplar), transformation is carried out by introducing a fusion polynucleotide of said polynucleotide and a polynucleotide encoding at least one transcription activation domain of a transcription factor. Examples of plants used for transformation in the present invention include, but are not limited to, plants belonging to Brassicaceae (e.g., *Arabidopsis thaliana*, cabbage, rapeseed), Gramineae (e.g., rice, maize, barley, wheat, switchgrass, sugar cane, sorghum), Solanaceae (e.g., tomato, eggplant, potato, tobacco), Leguminosae (e.g., soybean, garden pea, bush bean), Convolvulaceae (e.g., sweet potato), Compositae (e.g., sunflower), Euphorbiaceae (e.g., cassava, Jatropha), Rosaceae (e.g., strawberry), and *Salix* (e.g., poplar). Terrestrial plants, including gymnosperms, ferns, and mosses, can also be generally used.

Examples of plant materials to be subjected to transformation in the present invention include: plant organs such as stems, leaves, seeds, embryos, ovules, ovaries and shoot apices; plant tissues such as anthers and pollens, and the sections thereof; undifferentiated calluses; and cultured plant cells such as protoplasts which are prepared by removing cell walls from the above by enzyme treatment. When the in planta method is employed, an imbibed seed or a whole plant body can be utilized.

According to the present invention, the term "transgenic plant" means any one of a whole plant body, a plant organ (e.g., leaf, petal, stem, root, grain or seed), a plant tissue (e.g., epidermis, phloem, parenchyma, xylem, or vascular bundle), or a cultured plant cell (e.g., callus).

When a cultured plant cell is to be used, an organ or an individual may be regenerated according to a known tissue culture method in order to regenerate a transformant from a resulting transformed cell. A person skilled in the art can readily carry out such a procedure using a method that is commonly known as a method of regenerating a plant body from a plant cell. For example, a plant body can be regenerated from a plant cell in the following manner.

At the outset, when a plant tissue or a protoplast is used as a plant material to be subjected to transformation, it is cultured in a medium for callus formation that has been sterilized after adding, for example, inorganic elements, vitamins, carbon sources, saccharides as energy sources or plant growth regulators (plant hormones, such as auxin, cytokinin, gibberellin, abscisic acid, ethylene, or brassinosteroid) to form a dedifferentiated callus which proliferates in an unstructured manner (hereinafter, this process is referred to as "callus induction"). The thus formed callus is transferred to a fresh medium containing plant growth regulators such as auxin, and then further proliferated (or subcultured).

Callus induction is carried out on a solid medium such as agar, and subculture is carried out, for example, in a liquid medium. Thereby, the cultivation can be carried out efficiently and in large quantities in the respective cases. Subsequently, the callus proliferated by the aforementioned subculture is cultured under adequate conditions to induce redifferentiation of an organ (hereinafter referred to as "induction of redifferentiation"), and a complete plant body is regenerated in the end. The induction of redifferentiation can be carried out by adequately setting the types and quantities of respective ingredients such as plant growth regulators (e.g., auxin) and carbon sources in the medium, light, temperature and the like. Such induction of redifferentiation results in formation of adventitious embryo, adventitious root, adventitious bud, adventitious shoot and the like, which further leads to growth into a complete plant body. Alternatively, storage may be conducted in a state prior to the formation of a complete plant body (e.g., encapsulated artificial seed, dry embryo, or freeze-dried cell or tissue).

The transgenic plants of the present invention also include plant bodies of progenies obtained by sexual or asexual reproduction of plant bodies having a gene of interest being introduced (including plant bodies regenerated from transformed cells or calluses), and portions of tissues or organs of the progeny plants (seeds, protoplasts, and the like). The transgenic plant of the present invention can be produced in large quantities by obtaining a reproductive material such as a seed or a protoplast, from a plant body transformed by introduction of the target gene, and then cultivating or culturing the same.

The transgenic plant obtained as described above exhibits increased biomass per plant as a result of expression of the fusion polynucleotide. In the present invention, the term "biomass" refers to the amount of a plant body or a part thereof existing within an arbitrary space at a given time. The term is used to encompass substances, foods, materials, fuels, resources and the like derived from said plant or parts thereof. Specifically, increased biomass refers to hypertrophy of a subterranean stem (rhizom, corm, tuber, bulb), a terrestrial stem, a flowering stem or a vine, hypertrophy of a seed, acceleration of elongation of stem length, plant length, culm length or ear length, or enlargement of a source organ such as a leaf.

The transgenic plant obtained as described above also has environmental stress resistance. The term "environmental stress" generally means non-biological stress, such as dehydration stress, low temperature stress, high salt concentration stress or the like. The term "dehydration" means a state of water deprivation. The term "low temperature" refers to a state in which an organism species is exposed to a temperature lower than the optimal temperature for the life of the organism species (e.g., in case of *Arabidopsis thaliana*, it is exposed to a temperature of −20° C. to +21° C. for 1 hour to several weeks continuously). The term "high salt concentration" means a state in which treatment with NaCl at a concentration of 50 mM to 600 mM is carried out for 0.5 hour to several weeks continuously. A single type or a plurality of types of such environmental stresses may be applied.

Hereinafter, the present invention is described in greater detail with reference to the examples below, although the technical scope of the present invention is not limited to these examples.

Example 1

Construction of pBS-35S::PRR9-FLAG
pBS-35S::PRR7-FLAG, and pBS-35S::PRR5-FLAG
and Assay of Transcription Activation Function With the use of a vector prepared by incorporating the cauliflower mosaic virus-derived 35S transcription promoter, the FLAG peptide and the Nos transcription terminator into pBlueScript (Stratagene) (this vector is referred to as "pBS-35S::FLAG") (Biosci. Biotechnol. Biochem., 68 (9): 1966, 2004), vectors (pBS-35S::PRR9-FLAG, pBS-35S::PRR7-FLAG and pBS-35S::PRR5-FLAG) capable of expressing, under the control of the 35S transcription promoter, fusion proteins in which PRR9 (TAIR locus: At2g46790, SEQ ID NO: 9), PRR7 (TAIR locus: At5g02810, SEQ ID NO: 7) or PRR5 (TAIR locus: At5g24479, SEQ ID NO: 5) of *Arabidopsis thaliana* is connected in tandem to the FLAG peptide (Asp-Tyr-Lys-Asp-Asp-Asp-Asp-Lys: SEQ ID NO: 22) were constructed in the following manner.

The PRR5 gene reaches its peak expression 6 hours after dawn. Accordingly, *Arabidopsis thaliana* was subjected to sampling and freezing at the time to prepare mRNA and cDNA therefrom. RNA was extracted from a plant using the RNeasy Plant Minikit (Qiagen). cDNA synthesis by a reverse transcription reaction was carried out using SuperScript II (Invitrogen) and oligo dT20 as a primer. PRR5 cDNA was amplified by PCR using the resulting cDNA pool as a template and primers (5'-ACACTCTAGAATGACTAGTAGC-GAGGAAGTAG-3': SEQ ID NO: 23 and 5'-GTTGGATC-CTCTGGAGCTTGTGTGGATTGG-3': SEQ ID NO: 24). PCR was carried out using PrimeStar enzyme by allowing the mixture to stand at 94° C. for 2 minutes, and repeating a cycle of 94° C. for 15 seconds, 55° C. for 20 seconds, and 72° C. for 2 minutes 35 times. The amplified PRR5 cDNA fragment was treated with restriction enzymes XbaI (Takara) and BamHI (Takara) at 37° C. for 5 hours. pBS-35S::FLAG was also treated with XbaI and BamHI. PRR5 cDNA and pBS-35S::FLAG which had been treated with the restriction enzymes were connected to each other by a ligation reaction, the resultant was used to transform *Escherichia coli* DH5a (Takara), and a vector (pBS-35S::PRR5-FLAG) was recovered from a transformant. pBS-35S::PRR7-FLAG and pBS-35S::PRR9-FLAG were prepared in a similar manner. mRNA used for cloning was obtained from *Arabidopsis thaliana* 3 hours after dawn, PRR7 cDNA was amplified by PCR using primers (5'-CTTATCTAGAATGAATGCTAATGAGGAGGG-3': SEQ ID NO: 25 and 5'-GAGTCCATGGTGCTATCCT-CAATGTTTTTTATGTC-3': SEQ ID NO: 26), and PRR9 cDNA was amplified by PCR using primers (5'-CAAATCTA-GAATGGGGGAGATTGTGG-3': SEQ ID NO: 27 and 5'-GAAGTCCATGGTTGATTTTGTAGACGCGTCTG-3': SEQ ID NO: 28). The amplified PRR7 cDNA and PRR9 cDNA fragments were treated with restriction enzymes XbaI (Takara) and NcoI (Takara) at 37° C. for 5 hours. pBS-35S::FLAG was also treated with XbaI and NcoI. The PRR9 cDNA or PRR7 cDNA fragment and pBS-35S::FLAG which had been treated with the restriction enzymes were connected to each other by ligation reactions, the resultants were used to transform *Escherichia coli* DH5a (Takara), and vectors (pBS-35S::PRR9-FLAG and pBS-35S::PRR7-FLAG) were recovered from transformants.

Figure 2:
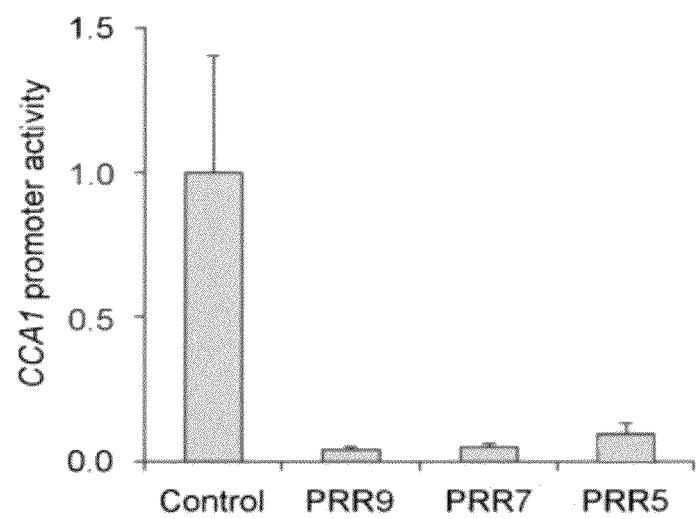
FIG. 2 shows the influence of PRR5, PRR7 and PRR9 on CCA1::LUC specific activity (CCA1 promoter activity).

A transient expression system in *Arabidopsis thaliana* was used to observe how the PRR9, PRR7 and PRR5 proteins regulate the CCA1 promoter. The pBS-35S::PRR9-FLAG, pBS-35S::PRR7-FLAG or pBS-35S::PRR5-FLAG vector (effector vector), the CCA1::LUC vector that expresses the luciferase gene under the control of the CCA1 promoter (reporter vector), and the 35S::RLUC vector that expresses *Renilla* luciferase under the control of the 35S promoter (reference vector) were mixed with each other in amounts of 0.8 µg, and gold particles (diameters: 1 µM) were coated therewith. With the use of particle bombardment (GE Healthcare), the resultants were transiently introduced into *Arabidopsis thaliana* plants that had been grown with 12 hours in the light (white light) and 12 hours in the dark for 2 weeks after germination. Luciferase activity and *Renilla* luciferase activity were measured at a given time 12 hours or more after the introduction (2 hours after the beginning of the light period) in accordance with the method of Yamaguchi et al. (The Plant Journal, 55: 652, 2008), and the luciferase activity/*Renilla* luciferase activity (the value for the control experiment is defined as 1) was evaluated as indicating CCA1 promoter activity. As a result, the introduction of the PRR9-FLAG, PRR7-FLAG and PRR5-FLAG proteins was found to suppress the CCA1 promoter more than the introduction of the FLAG protein (control) (FIG. 2). Since PRR9, PRR7 and PRR5 proteins physically interact with the CCA1 promoter in a plant body (The Plant Cell, vol. 22, 594-605, 2010), the PRR9, PRR7 and PRR5 proteins are considered to function as transcription repressors for the CCA1 promoter.

Example 2

Preparation of PRR5-VP32, PRR9-VP32, PRR7-VP32, PRR3-VP32 and PRR1-VP32 and Assay of Transcription Activation Function With the use of a vector prepared by incorporating a cauliflower mosaic virus-derived 35S transcription promoter and a Nos transcription terminator into pBlueScript (Stratagene) (this vector is referred to as "pBS-35S") (Biosci. Biotechnol. Biochem., 68 (9): 1966, 2004), a vector (pBS-35S::PRR5-VP32) capable of expressing, under the control of the 35S transcription promoter, a fusion protein in which PRR5 of *Arabidopsis thaliana* (TAIR locus: At5g24479, SEQ ID NO: 5) is connected in tandem to the VP16 transcription activation domain of a herpesvirus-derived transcription factor (the nucleotide sequence (SEQ ID NO: 11) encoding an amino acid sequence corresponding to positions 413 to 490 of the amino acid sequence GeneBank: ACM62271) was constructed in the following manner.

VP16 cDNA was amplified by PCR using pVP16 (Clontech) as a template and primers A (5'-GTTTACCATGGT-GAAAGTCGCCCCCCCG-3': SEQ ID NO: 29 and 5'-CTT-TAAGCTTCGGGAATTCCCCACCGTACTCGTC-3': SEQ ID NO: 30) or primers B (5'-CTTTAAGCTTAAAGTCGC-CCCCCCG-3': SEQ ID NO: 31 and 5'-CGAGAAAGCGGC-CGCTTACGGGAATTCCCCACCGTACTCGTC-3': SEQ ID NO: 32). The former VP16 cDNA is referred to as "VP16-1" and the latter is referred to as "VP16-2" for convenience. The reaction was carried out using PrimeStar enzyme (Takara) by allowing the mixture to stand at 94° C. for 2 minutes, and repeating a cycle of 94° C. for 15 seconds, 55° C. for 20 seconds, and 72° C. for 30 seconds 35 times. The amplified VP16-1 was treated with restriction enzymes NcoI (Takara) and HindIII (Takara) and the amplified VP16-2 was treated with HindIII and NotI (Takara) at 37° C. for 5 hours. Further, pBS-35S was treated with NcoI and NotI at 37° C. for 5 hours. VP16-1, VP16-2, and pBS-35S which had been treated with the restriction enzymes were connected to each other by a ligation reaction. The ligation reaction was carried out using Ligation High ver2 (Takara) in accordance with the attached instructions. The DNA solution subjected to ligation was used to transform *Escherichia coli* DH5a by the heat shock method. The transformed DH5a was selected on Luria-Bertani agar medium containing ampicillin (50 µg/ml). The resulting transformant was cultured in Luria-Bertani liquid medium containing ampicillin (50 µg/ml), and a vector was then recovered therefrom (this vector is referred to as "pBS-35S::VP32").

Figure 3:
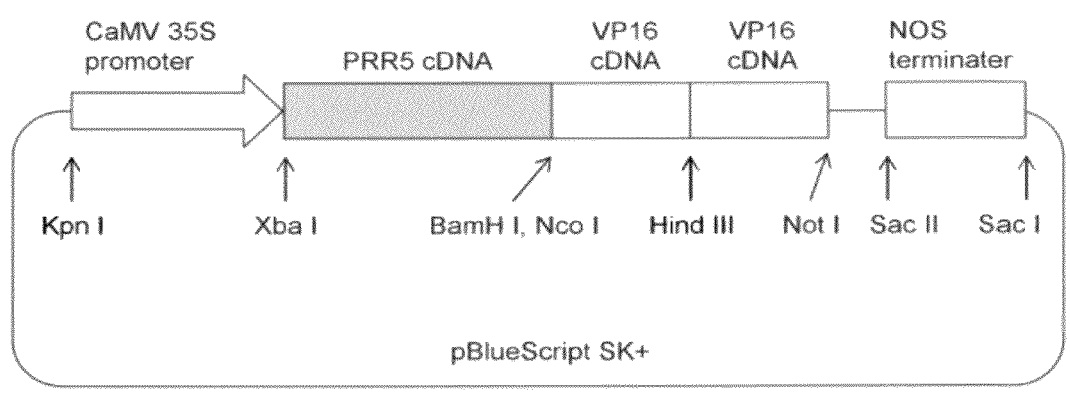
FIG. 3 shows the structure of the pBS-35S::PRR5-VP32 vector.

The PRR5 gene reaches its peak expression 6 hours after dawn. Accordingly, *Arabidopsis thaliana* was subjected to sampling and freezing at the time to prepare mRNA and cDNA therefrom. RNA was extracted from a plant using the RNeasy Plant Minikit (Qiagen). cDNA synthesis by a reverse transcription reaction was carried out using SuperScript II (Invitrogen) and oligo dT20 as a primer. PRR5 cDNA was amplified by PCR using the resulting cDNA pool as a template and primers (5'-ACACTCTAGAATGACTAGTAGC-GAGGAAGTAG-3': SEQ ID NO: 23 and 5'-GTTGGATC-CTCTGGAGCTTGTGTGGATTGG-3': SEQ ID NO: 24). PCR was carried out using PrimeStar enzyme by allowing the mixture to stand at 94° C. for 2 minutes, and repeating a cycle of 94° C. for 15 seconds, 55° C. for 20 seconds, and 72° C. for 2 minutes 35 times. The amplified PRR5 cDNA fragment was treated with restriction enzymes XbaI (Takara) and BamHI (Takara) at 37° C. for 5 hours. pBS-35S::VP32 was also treated with XbaI and BamHI. PRR5 cDNA and pBS-35S::VP32 which had been treated with the restriction enzymes were connected to each other by a ligation reaction, the resultant was used to transform *Escherichia coli* DH5a (Takara), and a vector (pBS-35S::PRR5-VP32, FIG. 3) was recovered from a transformant.

Figure 4:
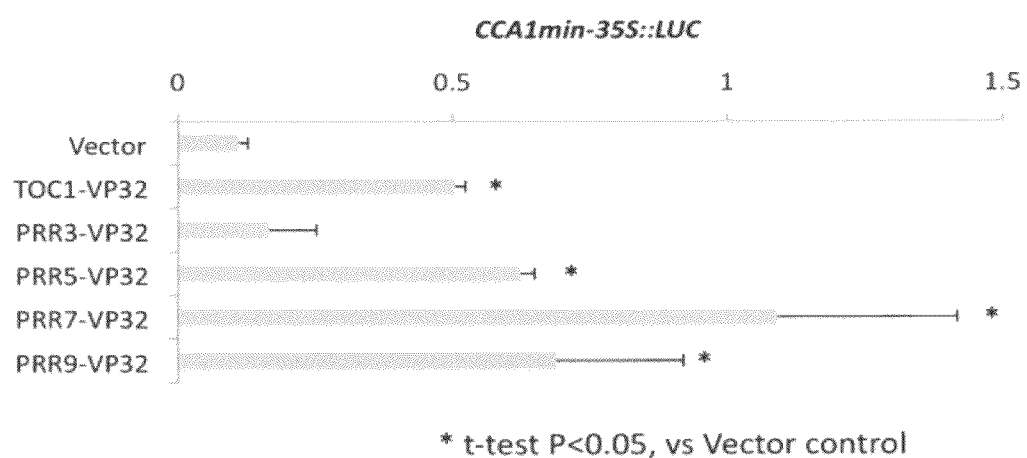
FIG. 4 shows the influence of TOC1-VP32, PRR3-VP32, PRR5-VP32, PRR7-VP32 and PRR9-VP32 on CCA1::LUC specific activity (CCA1 promoter activity).

Subsequently, a transient expression system in *Arabidopsis thaliana* was used to observe how the PRR5-VP32 protein regulates the CCA1 promoter. The pBS-35S::PRR5-VP32 vector (effector vector), the CCA1min-35S::LUC vector that expresses the luciferase gene under the control of the CCA1 promoter (reporter vector) [prepared by amplifying a region from −406 nt to −299 nt of the CCA1 promoter (where "0nt" represents the translation initiation site) with the use of the primers 5'-ACGCCAAGCTAAGCTTCTAGTATGTTGA-CATATGGC-3'(SEQ ID NO: 35) and 5'-GAAGGGTCT-TGCGATATCGCTACGGAAATGGAGAAATC-3' (SEQ ID NO: 36) to obtain CCA1min, and subjecting CCA1min to the In-Fusion reaction (Takara) to clone the same into HindIII and EcoRV restriction enzyme sites located upstream of the CaMV 35S promoter minimal region], and the 35S::RLUC vector (reference vector) that expresses *Renilla* luciferase under the control of the 35S promoter were mixed with each other in amounts of 0.8 μg, and gold particles (diameters: 1 μM) were coated therewith. With the use of particle bombardment (GE Healthcare), the resultants were transiently introduced into *Arabidopsis thaliana* plants that had been grown with 12 hours in the light (white light) and 12 hours in the dark for 2 weeks after germination. Luciferase activity and *Renilla* luciferase activity were measured at a given time 12 hours or more after the introduction (2 hours after the beginning of the light period) in accordance with the method of Yamaguchi et al. (The Plant Journal, 55: 652, 2008), and the luciferase activity/*Renilla* luciferase activity was evaluated as indicating CCA1 promoter activity. As a result, the introduction of the PRR5-VP32 protein was found to activate the CCA1 promoter more effectively than the introduction of the VP32 protein (FIG. 4). Since the PRR5 protein physically interacts with the CCA1 promoter in a plant body (The Plant Cell, vol. 22, 594-605, 2010), the PRR5-VP32 protein is considered to function as a transcription activator for the CCA1 promoter.

There are four genes homologous to the PRR5 gene in *Arabidopsis thaliana* (PRR9, PRR7, PRR3, and TOC1). Accordingly, whether or not a fusion of VP32 and a protein encoded by one of the genes (PRR-VP32)) would also be capable of activating the CCA1 promoter as in the case of PRR5-VP32 was examined.

PRR9 was amplified by PCR with the use of primers (5'-CACCATGGGGGAGATTGTGGTTTTAAG-3': SEQ ID NO: 37 and 5'-TGATTTTGTAGACGCGTCTG-3': SEQ ID NO: 38), and the resultant was TOPO-cloned into the pENTR-DTOPO vector (Invitrogen) (vector name: pENTR-DTOPO-PRR9).

PRR7 was amplified by PCR with the use of primers (5'-CACCATGAATGCTAATGAGGAGGG-3': SEQ ID NO: 39 and 5'-GCTATCCTCAATGTTTTTTATGTC-3': SEQ ID NO: 40), and the resultant was cloned into pENTR-DTOPO (vector name: pENTR-DTOPO-PRR7).

PRR3 was amplified by PCR with the use of primers (5'-CACCATGTGTTTTAATAACATTGAAACTGGTGATG-3': SEQ ID NO: 41 and 5'-ATTGTCTTCACTTCCTGATT-TATGATC-3': SEQ ID NO: 42), and the resultant was cloned into pENTR-DTOPO (vector name: pENTR-DTOPO-PRR3).

TOC1 was amplified by PCR with the use of primers (5'-CACCATGGATTTGAACGGTGAGTG-3': SEQ ID NO: 43 and 5'-AGTTCCCAAAGCATCATCC-3': SEQ ID NO: 44), and the resultant was cloned into pENTR-DTOPO (vector name: pENTR-DTOPO-TOC1).

On the other hand, pBS-35S::PRR5-VP32 was digested with XbaI and BamHI, the PRR5 sequence was removed by gel electrophoresis, and the vector portion (pBS-35S::VP32) was blunt-ended with T4 polymerase (Takara). The Reading Frame Cassette B DNA fragment was incorporated by a ligation reaction between the blunt ends with the use of the Gateway Vector Conversion System (pBS-35S::VP32-GW). With the use of LR reaction kit (Invitrogen), the PRR gene sequences were cloned from the respective pENTR-DTOPO-PRRs prepared as described above into pBS-35S::VP32-GW (pBS-35S::PRR-VP32). The resultants were used as effector vectors to assay the CCA1 promoter activities using the *Arabidopsis thaliana* transient expression system. As a result, transient overexpression of PRR9-VP32, PRR7-VP32, and TOC1-VP32 was found to be able to activate the CCA1 promoter (FIG. 4).

Example 3

Acquisition of *Arabidopsis thaliana* that Expresses PRR5-VP32

The pBS-35S::PRR5-VP32 vector DNA was treated with XbaI and NotI at 37° C. for 5 hours and the resultant was electrophoresed on agarose gel. The PRR5-VP32 fragment in the gel was visualized under UV light by EtBr staining, and a gel containing the fragment was excised using a razor. DNA was purified from the gel using NucleoSpin (Macherey-Nagel). The PRR5-VP32 fragment was cloned between the XbaI and NotI restriction enzyme sites of the pSK1 binary vector (DNA Res. 6: 407, 1999), and the resulting vector (pSK1-35S::PRR5-VP32) was used to transform *Agrobacterium tumefaciens* EHA105 by the heat shock method. Transformants were selected on Luria-Bertani agar medium containing rifampicin (25 μg/ml) and kanamycin (25 μg/ml). The resulting transformed EHA105 was cultured in Luria-Bertani liquid medium containing rifampicin (25 μg/ml) and kanamycin (25 μg/ml) at 30° C. for 24 hours and used to infect *Arabidopsis thaliana*. Infection was carried out by the vacuum infiltration method (CR Acad. Sci. Paris, Life Science, 316: 1194, 1993). *Arabidopsis thaliana* plants were grown in soil composed of a 1:1 mixture of vermiculite and culture soil, and inflorescences was directly dipped in the culture of EHA105 harboring pSK1-35S::PRR5-VP32. The resultant was placed in a desiccator, suctioned to 60 to 70 mmHg with the use of a vacuum pump, and then allowed to stand for 10 minutes at room temperature. The pot was transferred to a tray and covered with a plastic wrap to preserve the moisture. The wrap was removed on the following day, the plants were allowed to grow, and seeds were collected. The seeds were sowed on Murashige-Skoog agar medium containing 25 µg/ml of hygromycin, and plant individuals capable of growing were obtained as transgenic plants. Among the obtained plants, plants for which overexpression of PRR5-VP32 mRNA was observed were selected.

mRNA was quantified in the following manner. RNA was extracted from a plant using the RNeasy Plant Minikit. cDNA synthesis by a reverse transcription reaction was carried out using SuperScript II. Quantitative PCR was carried out using SYBR Green Extaq II (Takara) as a reaction mixture and the primers (5'-CTTCATCCTTCTAGTGCC-3': SEQ ID NO: 33 and 5'-GTCGTTTCTTCTTGGAGC-3': SEQ ID NO: 34). PCR products were detected and quantified using the ABI PRISM 7000 sequence detection system (ABI). The selected PRR5-VP32-expressing recombinants were allowed to self-pollinate, and plants homozygously comprising the recombinant DNA site were further selected. Selection was carried out using, as an indicator, growth of the plant on Murashige-Skoog agar medium containing 25 µg/ml of hygromycin.

Example 4

Biomass of *Arabidopsis thaliana* that Expresses PRR5-VP32

Figure 5:
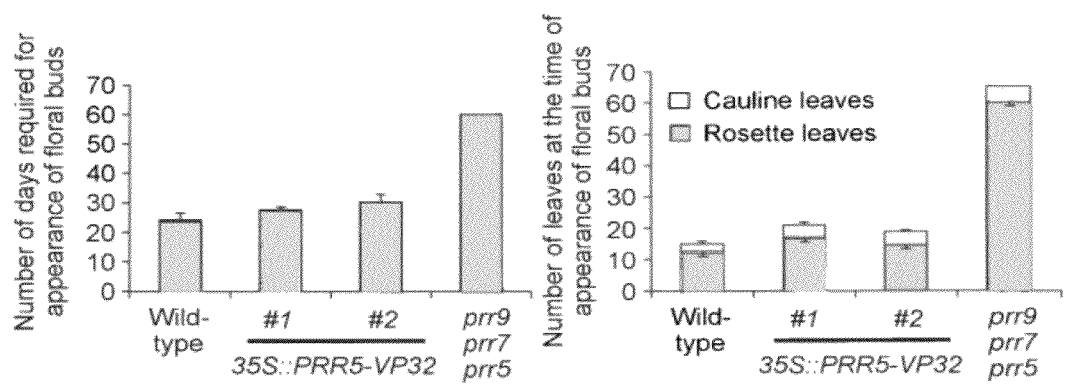
FIG. 5 shows the number of days required for the appearance of floral buds and the number of leaves at the time of appearance of floral buds for plant body expressing PRR5-VP32, wild-type plant, and the prr9 prr7 prr5 triple mutant.

The homozygous *Arabidopsis thaliana* plants harboring 35S::PRR5-VP32, prr9 prr7 prr5 triple mutants, and wild-type plants were allowed to grow on rock wool using a ½ diluted MGRL hydroponic solution (Plant Physiol., 99: 263, 1992) with 16 hours in the light and 8 hours in the dark. While floral bud formation of the plants expressing 35S::PRR5-VP32 delayed a little and the number of leaves at the time of floral bud formation was increased as compared with that of wild-type plants, the degrees of the delay and the increase were not so great as the cases of the prr9 prr7 prr5 triple mutants (FIG. 5). The fact that floral bud formation is not greatly delayed means that plant maturation would not be delayed. Accordingly, it can be said that the phenotypes are advantageous for acquisition of biomaterials.

Figure 6:
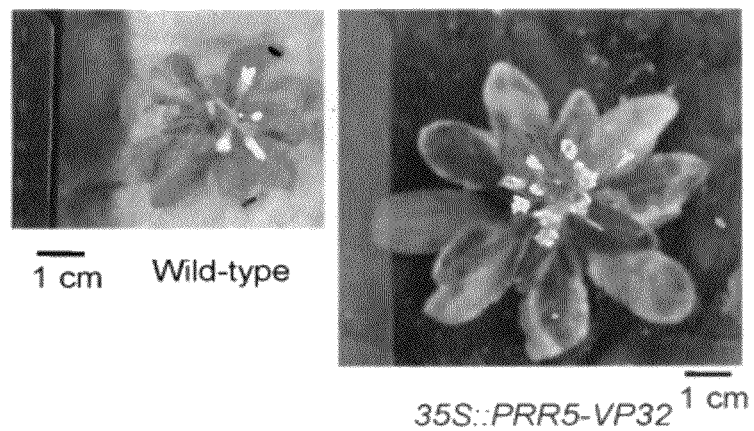
FIG. 6 shows the morphology of plant body expressing PRR5-VP32 and wild-type plant at the time of floral bud formation (the same growth stage).
Figure 7:
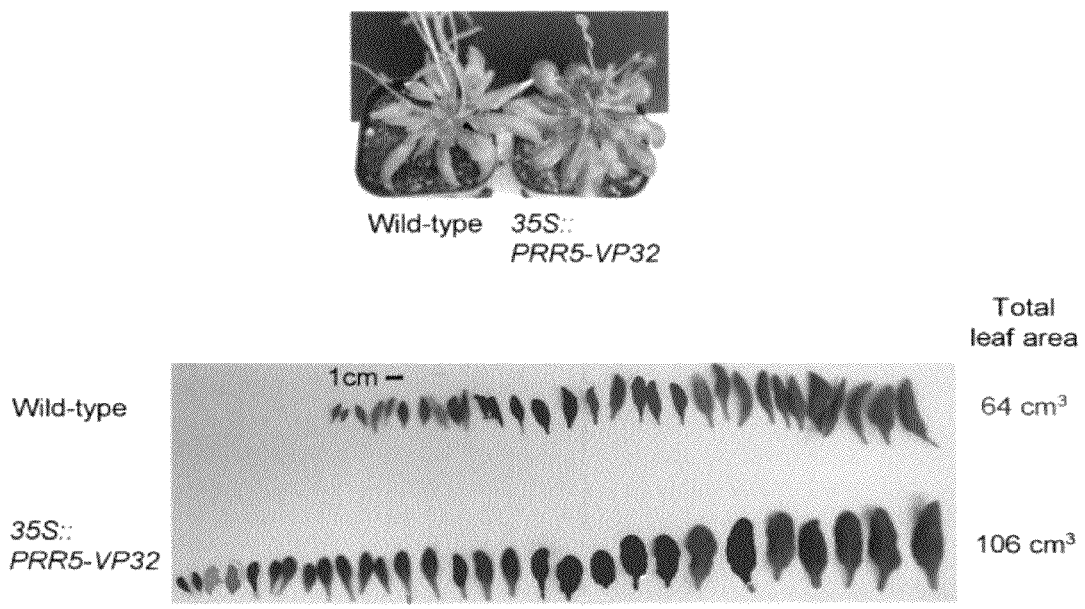
FIG. 7 shows the morphology (the upper part) and the leaf area (the lower part) of plant body expressing PRR5-VP32 and wild-type plant 38 days after budding (the same number of days of growth).
Figure 8:
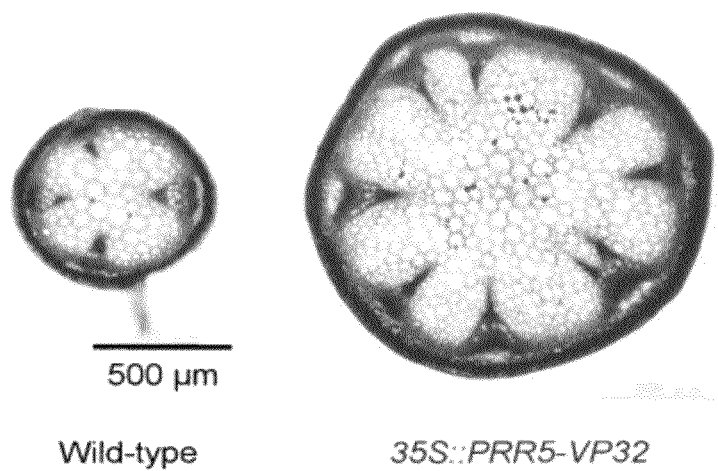
FIG. 8 shows cross-sectional views of the flowering stems of plant body expressing PRR5-VP32 and wild-type plant.

Further, the homozygous *Arabidopsis thaliana* plants harboring 35S::PRR5-VP32 and wild-type plants were allowed to grow on rock wool using a ½ diluted MGRL hydroponic solution (Plant Physiol., 99: 263, 1992) with 16 hours in the light and 8 hours in the dark. The plant bodies were photographed when the flowering stem lengths reached 8 cm (i.e., at the same growth stage). When the total leaf area per individual was measured using Image J (http://rsbweb.nih.gov/ij/), the leaf area of plant bodies expressing 35S::PRR5-VP32 was found to be about twice as large as that of wild-type plants (FIG. 6). Also, when the total leaf area per individual was measured using Image J 38 days after germination (i.e., after the same growth period in days), the leaf area of the plant body expressing PRR5-VP32 was found to be 1.7 to 1.8 times as large as that of wild-type plants (FIG. 7). Further, when the flowering stems reached a height of approximately 20 cm, the flowering stems were cut with a razor at a position between the axillary buds closest and second closest to the ground, the flowering stems were soaked in a staining solution (0.5% alcian blue and 1.0% safranin) for 5 minutes, and decolored with water, and the resulting cross sections were observed under a microscope (FIG. 8). As a result of the measurement of cross section areas of flowering stems using Image J, the cross sectional area of the flowering stem of the plant body expressing PRR5-VP32 was found to have increased by 4-fold or more as compared with the area of wild-type plant.

It is suggested that the above is caused by the increased number of cells that form flowering stems and the increased shoot apex meristems that constitute flowering stems. Such phenotypes were also observed in independent transformants (i.e., lines having different recombinant DNA sites on chromosomes).

Example 5

Environmental Stress Resistance of *Arabidopsis thaliana* that Expresses PRR5-VP32

(1) Salt Stress Resistance of Plant that Expresses PRR5-VP32

Figure 9:
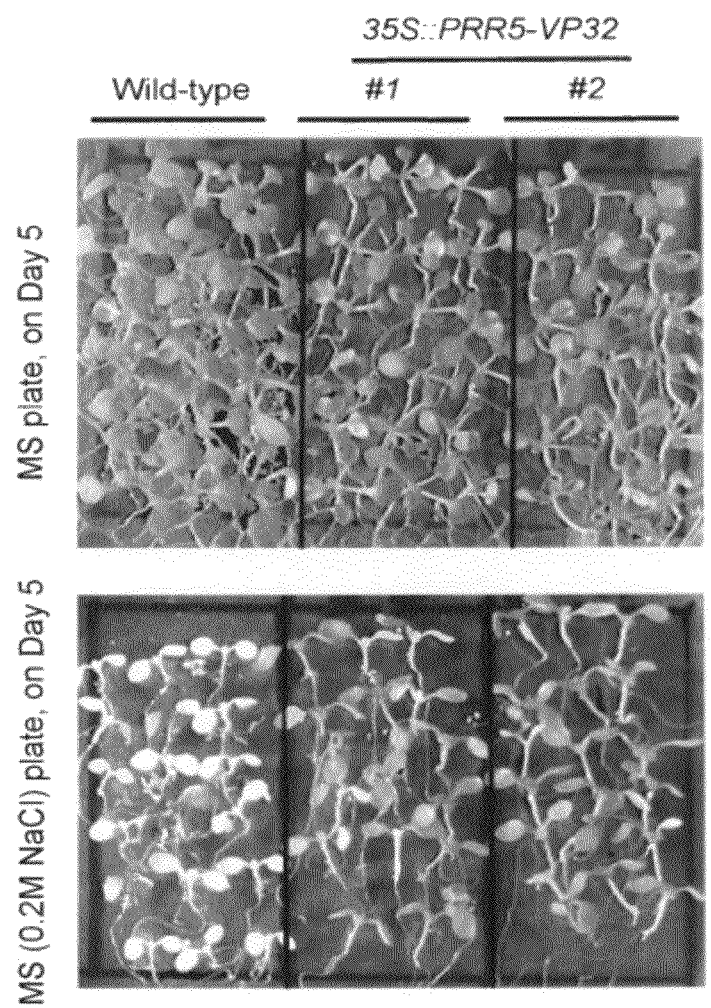
FIG. 9 shows the results of salt stress resistance tests for plant body expressing PRR5-VP32 and wild-type plant.

The homozygous *Arabidopsis thaliana* plants harboring 35S::PRR5-VP32 and wild-type plants were allowed to grow on MS medium with 16 hours in the light and 8 hours in the dark for 6 days and then transferred to salt stress medium. Normal MS medium or MS medium containing 0.2M NaCl was used. The plant bodies were photographed 5 days after the transfer. While the leaves of wild-type plants became white, plants expressing 35S::PRR5-VP32 remained green. This indicates that plants expressing 35S::PRR5-VP32 have higher salt resistance than wild-type plants (FIG. 9).

(2) Dehydration Stress Resistance of Plant that Expresses PRR5-VP32

Figure 10:
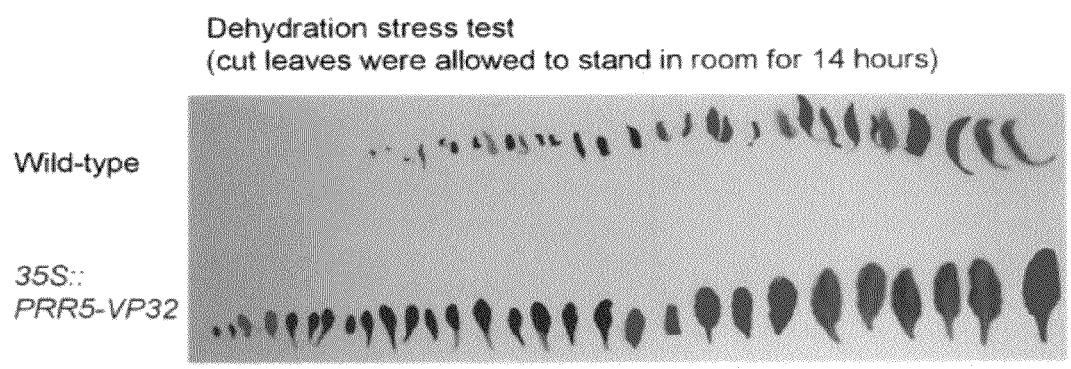
FIG. 10 shows the results of dehydration stress resistance tests for plant body expressing PRR5-VP32 and wild-type plant.

The homozygous *Arabidopsis thaliana* plants harboring 35S::PRR5-VP32 and wild-type plants were allowed to grow in soil composed of a 1:1 mixture of vermiculite and culture soil with 16 hours in the light and 8 hours in the dark for 38 days. Rosette leaves were cut from the plant bodies and allowed to stand in a room at 25° C. for 14 hours, and the plant bodies were then photographed. The leaves cut from the plants expressing 35S::PRR5-VP32 contained more water than those of wild-type plants (FIG. 10).

(3) Low Temperature Stress Resistance of Plant that Expresses PRR5-VP32

Figure 11:
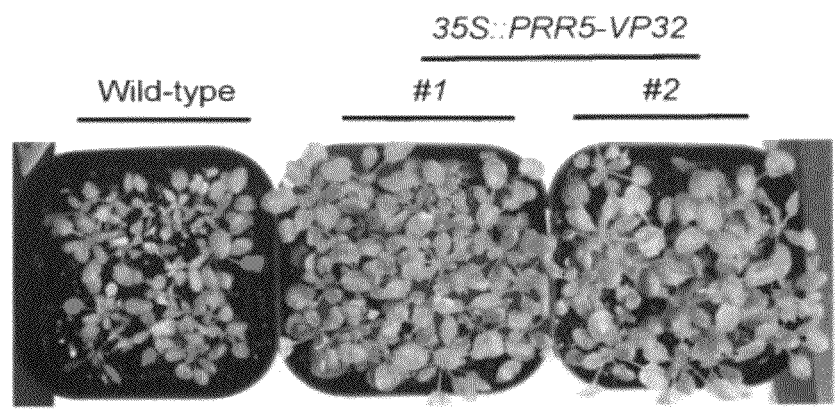
FIG. 11 shows the results of low temperature stress resistance tests for plant body expressing PRR5-VP32 and wild-type plant.

The homozygous *Arabidopsis thaliana* plants harboring 35S::PRR5-VP32 and wild-type plants were allowed to grow in soil composed of a 1:1 mixture of vermiculite and culture soil with 16 hours in the light and 8 hours in the dark for 26 days, placed in a thermostat-humidistat incubator set at −5° C. (Atmos Chamber, SANYO) for 24 hours, and then returned to the normal growth conditions. The plant bodies were photographed 5 days later. The plants expressing 35S::PRR5-VP32 were found to be more resistant to low temperature stress than wild-type plants (FIG. 11).

Example 6

Acquisition of Rice that Expresses PRR5

PCR was carried out using pBS-35S::PRR5-FLAG prepared in Example 1 as a template, the primers (5'-AGAAGTCGACTCTAGATGACTAGTAGCGAGGAAG-3': SEQ ID NO: 45 and 5'-TCGAGCTCGGTACCCTTACTTGTCGT-CATCGTCTTTG-3': SEQ ID NO: 46), and PrimeStar enzyme to amplify the PRR5-FLAG sequence, and the resultant was incorporated between the XbaI restriction enzyme site and the SmaI restriction enzyme site of the pACT vector (Hirose et al., Plant Cell Physiol., vol. 48, 523-539, 2007) using the In-Fusion reaction (Takara) (pACT::PRR5-FLAG).

The pACT::PRR5-FLAG vector was used to transform *Agrobacterium* EHA105. Rice calluses were infected with the transformed *Agrobacterium* by the *Agrobacterium* method. The fully ripened and unhulled seeds (100 to 120 grains) were soaked in a sterilization solution containing sodium hypochlorite, and the solution was slowly stirred for 30 minutes to sterilize the seeds. The seeds were thoroughly washed with sterile water and aseptically placed in callus induction medium (N6D medium, Hirose et al., Plant Cell Physiol., vol. 48, 523-539, 2007) in amounts of 10 seeds per petri dish, and cultured with 12.5 hours in the light at 28° C. and for 11.5 hours in the dark at 24° C. The albumen and shoot portions were removed from the seeds 3 weeks later, only calluses derived from scutellum were transferred to a fresh callus induction medium (N6D medium), and cultured for 3 days. The transformed *Agrobacterium* cells were applied to AB medium (Hirose et al., Plant Cell Physiol., vol. 48, 523-539, 2007) containing 50 µg/ml of kanamycin on the same day, and cultured at 28° C. with shading. *Agrobacterium* cells that had grown on AB medium were scraped off and suspended in a coexistence medium containing 20 µg/ml of acetosyringone (AAM solution, Hirose et al., Plant Cell Physiol., vol. 48, 523-539, 2007)3 days later, and OD600 of the suspension was adjusted to 0.15 to 0.2. The calluses that had been pre-cultured for 3 days were soaked in the *Agrobacterium* suspension, and the suspension was agitated by turning upside down for 1.5 minutes. After an excess *Agrobacterium* suspension was removed, the calluses were placed in a co-culture medium (2N6-AS medium, Hirose et al., Plant Cell Physiol., vol. 48, 523-539, 2007) containing 20 µg/ml of acetosyringone in amounts of 10 calluses per petri dish. *Agrobacterium* cells were co-cultured with calluses at 28° C. with shading. After 3 days, in order to remove the grown *Agrobacterium* cells, the calluses were collected in two 50-ml tubes, and the tubes were subjected to three rounds of 5-minutes agitation using a rotator with sterile water being poured and three rounds of 5-minutes agitation with sterile water containing 500 µg/ml of carbenicillin. The resultants were placed in a selection medium (N6D medium) containing 500 µg/ml of carbenicillin and 50 µg/ml of hygromycin in amounts of 10 calluses per petri dish, and cultured at 28° C. for 3 weeks. Thereafter, all the calluses were transferred to a redifferentiation medium containing 250 µg/ml of carbenicillin and 50 µg/ml of hygromycin, and the medium was exchanged with a fresh medium every 3 weeks until redifferentiation took place. The shoots that had been redifferentiated to approximately 2 cm were obtained approximately 1.5 months after the transfer of calluses to the redifferentiation medium. The resultants were transferred to Agripots in which a hormone-free medium containing 200 µg/ml of carbenicillin and 50 µg/ml of hygromycin had been poured and solidified to promote rooting, and the plants were allowed to grow to approximately 12 cm.

It was confirmed by Western blotting that ACT-PRR5-FLAG was introduced into the nuclear genome of the shoot cell and the PRR5-FLAG protein was actually expressed. The shoots having the pACT vector being introduced into the genome were also obtained.

Example 7

Biomass of rice That Expresses PRR5

Figure 12:
FIG. 12 shows the morphology of plant body expressing PRR5 (rice).

The shoots having pACT-PRR5-FLAG or pACT being introduced were simultaneously transferred into soil in a pod (Akadama tsuchi with 1 g of a slow-acting fertilizer Temairazu per pod), and the plants were then allowed to grow under short-day conditions (from December to March) in a greenhouse with 12 hours in the light at 30° C. and 12 hours in the dark at 25° C. A mixture of sunlight and electric light was used for lighting. The rice plants having pACT-PRR5-FLAG being introduced exhibited phenotypes of greater numbers of stems and increased heights as compared with the rice plants having pACT being introduced (FIG. 12). That is, the biomass was increased. These phenotypes were also observed in independent transformants (lines exhibiting different recombinant DNA sites on chromosomes).

All publications, patents, and patent applications cited herein are incorporated herein by reference in their entirety.

INDUSTRIAL APPLICABILITY

According to the present invention, a transgenic plant exhibiting increased biomass and improved environmental stress resistance is obtained. Increased biomass of plants leads to increased biofuel production, and conferring of environmental stress resistance enables plants to grow in a severe environment (e.g., dehydration, low temperature, or high salt concentration). In addition, the transgenic plant of the present invention can be prepared in a simple and easy manner without a complicated procedure for preparing a PRR gene multiple mutant.

SEQUENCE LISTING

```
<160> NUMBER OF SEQ ID NOS: 46

<210> SEQ ID NO 1
<211> LENGTH: 1857
<212> TYPE: DNA
<213> ORGANISM: Arabidopsis thaliana
<220> FEATURE:
<221> NAME/KEY: CDS
<222> LOCATION: (1)..(1857)

<400> SEQUENCE: 1 atg gat ttg aac ggt gag tgt aaa gga gga gat ggg ttt att gat aga      48
Met Asp Leu Asn Gly Glu Cys Lys Gly Gly Asp Gly Phe Ile Asp Arg
1               5                   10                  15 agc aga gtc agg att ttg ctt tgt gac aat gat tcc acg agt ttg gga      96
Ser Arg Val Arg Ile Leu Leu Cys Asp Asn Asp Ser Thr Ser Leu Gly
            20                  25                  30 gag gtt ttt act ctc ctt tca gag tgt tct tat caa gtg act gca gtg     144
Glu Val Phe Thr Leu Leu Ser Glu Cys Ser Tyr Gln Val Thr Ala Val
        35                  40                  45
```

| | | |
|---|---|---|
| aaa tca gca agg cag gtg att gat gca ctt aat gca gag gga cct gat<br>Lys Ser Ala Arg Gln Val Ile Asp Ala Leu Asn Ala Glu Gly Pro Asp<br>50                     55                   60 | | 192 |
| atc gat ata ata ctg gcg gaa att gat ctc cca atg gct aag ggt atg<br>Ile Asp Ile Ile Leu Ala Glu Ile Asp Leu Pro Met Ala Lys Gly Met<br>65                 70                   75                   80 | | 240 |
| aag atg ctg agg tac atc aca cga gac aaa gat ctt cgc aga atc cct<br>Lys Met Leu Arg Tyr Ile Thr Arg Asp Lys Asp Leu Arg Arg Ile Pro<br>                 85                   90                   95 | | 288 |
| gtg ata atg atg tcg agg caa gac gaa gtc cct gtc gtt gta aag tgc<br>Val Ile Met Met Ser Arg Gln Asp Glu Val Pro Val Val Val Lys Cys<br>                100                     105                   110 | | 336 |
| ttg aag cta ggt gca gct gac tac ctt gtg aag cct ctt cgc acc aac<br>Leu Lys Leu Gly Ala Ala Asp Tyr Leu Val Lys Pro Leu Arg Thr Asn<br>       115                   120                   125 | | 384 |
| gag ctt ctg aac ttg tgg aca cac atg tgg aga aga aga cgc atg cta<br>Glu Leu Leu Asn Leu Trp Thr His Met Trp Arg Arg Arg Arg Met Leu<br>130                   135                   140 | | 432 |
| gga ctt gct gag aag aat atg ttg agc tat gat ttt gat ctt gtg gga<br>Gly Leu Ala Glu Lys Asn Met Leu Ser Tyr Asp Phe Asp Leu Val Gly<br>145                   150                   155                   160 | | 480 |
| tct gat caa agt gat cca aac aca aat agt acc aac ctg ttc tct gac<br>Ser Asp Gln Ser Asp Pro Asn Thr Asn Ser Thr Asn Leu Phe Ser Asp<br>                165                   170                   175 | | 528 |
| gac aca gat gat aga agt ctt agg tcc acc aac cca cag aga gga aat<br>Asp Thr Asp Asp Arg Ser Leu Arg Ser Thr Asn Pro Gln Arg Gly Asn<br>                    180                   185                   190 | | 576 |
| tta agt cac cag gaa aat gag tgg tct gtt gct act gct cct gtt cat<br>Leu Ser His Gln Glu Asn Glu Trp Ser Val Ala Thr Ala Pro Val His<br>       195                   200                   205 | | 624 |
| gct cgt gat ggt ggt ctt ggt gct gat gga aca gcc act tct tct ctt<br>Ala Arg Asp Gly Gly Leu Gly Ala Asp Gly Thr Ala Thr Ser Ser Leu<br>210                   215                   220 | | 672 |
| gct gtt act gct ata gag cct cca ttg gat cat ctt gct ggg tct cac<br>Ala Val Thr Ala Ile Glu Pro Pro Leu Asp His Leu Ala Gly Ser His<br>225                   230                   235                   240 | | 720 |
| cat gag cca atg aaa aga aat agt aat cca gcg caa ttt tct tca gca<br>His Glu Pro Met Lys Arg Asn Ser Asn Pro Ala Gln Phe Ser Ser Ala<br>                245                   250                   255 | | 768 |
| ccg aag aaa agt aga ttg aag atc gga gag tcc tct gct ttc ttt aca<br>Pro Lys Lys Ser Arg Leu Lys Ile Gly Glu Ser Ser Ala Phe Phe Thr<br>                    260                   265                   270 | | 816 |
| tat gtc aaa tct act gtc ctt aga act aac ggt cag gat cct cct ctt<br>Tyr Val Lys Ser Thr Val Leu Arg Thr Asn Gly Gln Asp Pro Pro Leu<br>       275                   280                   285 | | 864 |
| gtc gat gga aat ggc tca ctt cat ctt cat cgg ggt ttg gcg gag aag<br>Val Asp Gly Asn Gly Ser Leu His Leu His Arg Gly Leu Ala Glu Lys<br>290                   295                   300 | | 912 |
| ttt caa gtg gtg gct agt gaa ggg atc aac aac acc aaa caa gca cgc<br>Phe Gln Val Val Ala Ser Glu Gly Ile Asn Asn Thr Lys Gln Ala Arg<br>305                   310                   315                   320 | | 960 |
| aga gca aca cca aaa tct act gtc ctt aga act aac ggt cag gat cct<br>Arg Ala Thr Pro Lys Ser Thr Val Leu Arg Thr Asn Gly Gln Asp Pro<br>                325                   330                   335 | | 1008 |
| cct ctt gtc aat gga aat ggc tca cat cat ctt cat cgg ggt gcg gcg<br>Pro Leu Val Asn Gly Asn Gly Ser His His Leu His Arg Gly Ala Ala<br>                340                   345                   350 | | 1056 |
| gaa aag ttt caa gtg gtg gct agt gaa ggg atc aac aac acc aaa caa<br>Glu Lys Phe Gln Val Val Ala Ser Glu Gly Ile Asn Asn Thr Lys Gln | | 1104 |

```
                355                 360                 365
gca cac aga agt aga ggg acc gag caa tac cat tct caa gga gag acc      1152
Ala His Arg Ser Arg Gly Thr Glu Gln Tyr His Ser Gln Gly Glu Thr
370                 375                 380 ttg cag aat ggc gcc agc tat cca cat tcc ctt gag cgg tca cgc acg      1200
Leu Gln Asn Gly Ala Ser Tyr Pro His Ser Leu Glu Arg Ser Arg Thr
385                 390                 395                 400 ctt ccc aca tca atg gaa tct cat ggt agg aac tac caa gag ggc aat      1248
Leu Pro Thr Ser Met Glu Ser His Gly Arg Asn Tyr Gln Glu Gly Asn
                405                 410                 415 atg aat att ccc caa gtt gct atg aac aga agt aaa gat tcg tct caa      1296
Met Asn Ile Pro Gln Val Ala Met Asn Arg Ser Lys Asp Ser Ser Gln
        420                 425                 430 gtt gat gga tcg ggt ttc tct gca cca aat gcc tat cct tac tat atg      1344
Val Asp Gly Ser Gly Phe Ser Ala Pro Asn Ala Tyr Pro Tyr Tyr Met
435                 440                 445 cat ggg gtc atg aac caa gtt atg atg caa tca gca gcc atg atg cct      1392
His Gly Val Met Asn Gln Val Met Met Gln Ser Ala Ala Met Met Pro
450                 455                 460 caa tat ggt cat caa att cct cat tgc caa cca aat cat ccg aat gga      1440
Gln Tyr Gly His Gln Ile Pro His Cys Gln Pro Asn His Pro Asn Gly
465                 470                 475                 480 atg acg gga tat cct tac tac cac cac cca atg aac aca tct ttg cag      1488
Met Thr Gly Tyr Pro Tyr Tyr His His Pro Met Asn Thr Ser Leu Gln
                485                 490                 495 cat agt cag atg tct tta cag aat ggt cag atg tct atg gtt cat cat      1536
His Ser Gln Met Ser Leu Gln Asn Gly Gln Met Ser Met Val His His
        500                 505                 510 tct tgg tca ccg gca gga aat ccg cct tct aat gag gtg agg gta aat      1584
Ser Trp Ser Pro Ala Gly Asn Pro Pro Ser Asn Glu Val Arg Val Asn
515                 520                 525 aaa ctt gac aga aga gag gaa gct ctg ctg aaa ttc aga cgt aaa agg      1632
Lys Leu Asp Arg Arg Glu Glu Ala Leu Leu Lys Phe Arg Arg Lys Arg
530                 535                 540 aac caa cgt tgt ttt gat aag aag att agg tat gtg aat agg aaa cgc      1680
Asn Gln Arg Cys Phe Asp Lys Lys Ile Arg Tyr Val Asn Arg Lys Arg
545                 550                 555                 560 ctt gct gag agg aga ccc cgc gtt aag ggt cag ttt gtt agg aag atg      1728
Leu Ala Glu Arg Arg Pro Arg Val Lys Gly Gln Phe Val Arg Lys Met
                565                 570                 575 aac ggc gtg aat gtt gat tta aat gga cag cct gac tct gct gac tat      1776
Asn Gly Val Asn Val Asp Leu Asn Gly Gln Pro Asp Ser Ala Asp Tyr
        580                 585                 590 gat gac gag gaa gag gag gaa gaa gaa gaa gaa gag gag aac cgg gat      1824
Asp Asp Glu Glu Glu Glu Glu Glu Glu Glu Glu Glu Asn Arg Asp
595                 600                 605 tca tct cct cag gat gat gct ttg gga act tga                          1857
Ser Ser Pro Gln Asp Asp Ala Leu Gly Thr
        610                 615

<210> SEQ ID NO 2
<211> LENGTH: 618
<212> TYPE: PRT
<213> ORGANISM: Arabidopsis thaliana

<400> SEQUENCE: 2

Met Asp Leu Asn Gly Glu Cys Lys Gly Gly Asp Gly Phe Ile Asp Arg
1               5                   10                  15

Ser Arg Val Arg Ile Leu Leu Cys Asp Asn Asp Ser Thr Ser Leu Gly
            20                  25                  30
```

```
Glu Val Phe Thr Leu Leu Ser Glu Cys Ser Tyr Gln Val Thr Ala Val
             35                  40                  45

Lys Ser Ala Arg Gln Val Ile Asp Ala Leu Asn Ala Glu Gly Pro Asp
 50                  55                  60

Ile Asp Ile Ile Leu Ala Glu Ile Asp Leu Pro Met Ala Lys Gly Met
 65                  70                  75                  80

Lys Met Leu Arg Tyr Ile Thr Arg Asp Lys Asp Leu Arg Arg Ile Pro
                 85                  90                  95

Val Ile Met Met Ser Arg Gln Asp Glu Val Pro Val Val Lys Cys
                100                 105                 110

Leu Lys Leu Gly Ala Ala Asp Tyr Leu Val Lys Pro Leu Arg Thr Asn
            115                 120                 125

Glu Leu Leu Asn Leu Trp Thr His Met Trp Arg Arg Arg Met Leu
            130                 135                 140

Gly Leu Ala Glu Lys Asn Met Leu Ser Tyr Asp Phe Asp Leu Val Gly
145                 150                 155                 160

Ser Asp Gln Ser Asp Pro Asn Thr Asn Ser Thr Asn Leu Phe Ser Asp
                165                 170                 175

Asp Thr Asp Asp Arg Ser Leu Arg Ser Thr Asn Pro Gln Arg Gly Asn
            180                 185                 190

Leu Ser His Gln Glu Asn Glu Trp Ser Val Ala Thr Ala Pro Val His
            195                 200                 205

Ala Arg Asp Gly Gly Leu Gly Ala Asp Gly Thr Ala Thr Ser Ser Leu
            210                 215                 220

Ala Val Thr Ala Ile Glu Pro Pro Leu Asp His Leu Ala Gly Ser His
225                 230                 235                 240

His Glu Pro Met Lys Arg Asn Ser Asn Pro Ala Gln Phe Ser Ser Ala
                245                 250                 255

Pro Lys Lys Ser Arg Leu Lys Ile Gly Glu Ser Ser Ala Phe Phe Thr
            260                 265                 270

Tyr Val Lys Ser Thr Val Leu Arg Thr Asn Gly Gln Asp Pro Pro Leu
            275                 280                 285

Val Asp Gly Asn Gly Ser Leu His Leu His Arg Gly Leu Ala Glu Lys
            290                 295                 300

Phe Gln Val Val Ala Ser Glu Gly Ile Asn Asn Thr Lys Gln Ala Arg
305                 310                 315                 320

Arg Ala Thr Pro Lys Ser Thr Val Leu Arg Thr Asn Gly Gln Asp Pro
                325                 330                 335

Pro Leu Val Asn Gly Asn Gly Ser His His Leu His Arg Gly Ala Ala
            340                 345                 350

Glu Lys Phe Gln Val Val Ala Ser Glu Gly Ile Asn Asn Thr Lys Gln
            355                 360                 365

Ala His Arg Ser Arg Gly Thr Glu Gln Tyr His Ser Gln Gly Glu Thr
            370                 375                 380

Leu Gln Asn Gly Ala Ser Tyr Pro His Ser Leu Glu Arg Ser Arg Thr
385                 390                 395                 400

Leu Pro Thr Ser Met Glu Ser His Gly Arg Asn Tyr Gln Glu Gly Asn
                405                 410                 415

Met Asn Ile Pro Gln Val Ala Met Asn Arg Ser Lys Asp Ser Ser Gln
            420                 425                 430

Val Asp Gly Ser Gly Phe Ser Ala Pro Asn Ala Tyr Pro Tyr Tyr Met
            435                 440                 445
```

```
His Gly Val Met Asn Gln Val Met Met Gln Ser Ala Ala Met Met Pro
    450                 455                 460
Gln Tyr Gly His Gln Ile Pro His Cys Gln Pro Asn His Pro Asn Gly
465                 470                 475                 480
Met Thr Gly Tyr Pro Tyr Tyr His His Pro Met Asn Thr Ser Leu Gln
                485                 490                 495
His Ser Gln Met Ser Leu Gln Asn Gly Gln Met Ser Met Val His His
                500                 505                 510
Ser Trp Ser Pro Ala Gly Asn Pro Ser Asn Glu Val Arg Val Asn
            515                 520                 525
Lys Leu Asp Arg Arg Glu Glu Ala Leu Leu Lys Phe Arg Arg Lys Arg
    530                 535                 540
Asn Gln Arg Cys Phe Asp Lys Lys Ile Arg Tyr Val Asn Arg Lys Arg
545                 550                 555                 560
Leu Ala Glu Arg Arg Pro Arg Val Lys Gly Gln Phe Val Arg Lys Met
                565                 570                 575
Asn Gly Val Asn Val Asp Leu Asn Gly Gln Pro Asp Ser Ala Asp Tyr
            580                 585                 590
Asp Asp Glu Glu Glu Glu Glu Glu Glu Glu Glu Asn Arg Asp
    595                 600                 605
Ser Ser Pro Gln Asp Asp Ala Leu Gly Thr
    610                 615
```

```
<210> SEQ ID NO 3
<211> LENGTH: 1488
<212> TYPE: DNA
<213> ORGANISM: Arabidopsis thaliana
<220> FEATURE:
<221> NAME/KEY: CDS
<222> LOCATION: (1)..(1488)

<400> SEQUENCE: 3 atg tgt ttt aat aac att gaa act ggt gat gaa gtg gaa acc gag agg    48
Met Cys Phe Asn Asn Ile Glu Thr Gly Asp Glu Val Glu Thr Glu Arg
1               5                   10                  15 caa gtg ttt ggt tca tct gaa gaa gat gaa ttt cga gtt gaa gat act    96
Gln Val Phe Gly Ser Ser Glu Glu Asp Glu Phe Arg Val Glu Asp Thr
            20                  25                  30 gct aga aat acc aac aat gta cag att tct caa caa cag cag caa ccg   144
Ala Arg Asn Thr Asn Asn Val Gln Ile Ser Gln Gln Gln Gln Gln Pro
        35                  40                  45 cta gct cat gtt gtg aag tgg gag agg tat ctc cca gtt aga tcg ctt   192
Leu Ala His Val Val Lys Trp Glu Arg Tyr Leu Pro Val Arg Ser Leu
    50                  55                  60 aag gtt ctt ctg gtg gag aat gat gac tca aca cgc cat att gtt act   240
Lys Val Leu Leu Val Glu Asn Asp Asp Ser Thr Arg His Ile Val Thr
65                  70                  75                  80 gcc ctt tta aag aat tgc agc tat gaa gtt act gct gtt ccg gat gtc   288
Ala Leu Leu Lys Asn Cys Ser Tyr Glu Val Thr Ala Val Pro Asp Val
                85                  90                  95 ctt gaa gcc tgg aga att cta gaa gat gag aaa agt tgc att gat ctt   336
Leu Glu Ala Trp Arg Ile Leu Glu Asp Glu Lys Ser Cys Ile Asp Leu
            100                 105                 110 gtc tta aca gag gtt gac atg cct gtg cat tca gga acc ggt ctg ctg   384
Val Leu Thr Glu Val Asp Met Pro Val His Ser Gly Thr Gly Leu Leu
        115                 120                 125 tcc aag att atg agc cat aag aca ctt aag aac atc ccc gtc ata atg   432
Ser Lys Ile Met Ser His Lys Thr Leu Lys Asn Ile Pro Val Ile Met
    130                 135                 140
```

```
atg tca tca cat gat tct atg gtt ctg gtc ttt aag tgt ttg tcg aat      480
Met Ser Ser His Asp Ser Met Val Leu Val Phe Lys Cys Leu Ser Asn
145                 150                 155                 160 ggt gct gtt gat ttt ctc gtg aaa ccc att aga aag aac gaa cta aag      528
Gly Ala Val Asp Phe Leu Val Lys Pro Ile Arg Lys Asn Glu Leu Lys
                165                 170                 175 aat ctt tgg caa cat gtc tgg aga aga tgt cac agc tct agc gga agc      576
Asn Leu Trp Gln His Val Trp Arg Arg Cys His Ser Ser Ser Gly Ser
            180                 185                 190 gga agt gag agt gga ata cat gac aag aag tcg gta aaa cct gaa agc      624
Gly Ser Glu Ser Gly Ile His Asp Lys Lys Ser Val Lys Pro Glu Ser
        195                 200                 205 acc caa ggg tca gaa aat gat gcc agc atc agt gat gaa cac agg aat      672
Thr Gln Gly Ser Glu Asn Asp Ala Ser Ile Ser Asp Glu His Arg Asn
    210                 215                 220 gaa agt ggg agt agt ggt ggt ttg agt aac caa gat ggt ggg agt gat      720
Glu Ser Gly Ser Ser Gly Gly Leu Ser Asn Gln Asp Gly Gly Ser Asp
225                 230                 235                 240 aac ggg agt gga act cag agt tct tgg aca aaa aga gcc agt gat act      768
Asn Gly Ser Gly Thr Gln Ser Ser Trp Thr Lys Arg Ala Ser Asp Thr
                245                 250                 255 aag agc acc tcg cct tca aat caa ttt ccc gat gca ccc aac aag aaa      816
Lys Ser Thr Ser Pro Ser Asn Gln Phe Pro Asp Ala Pro Asn Lys Lys
            260                 265                 270 gga acc tat gaa aat gga tgt gca cat gtt aat aga ctg aag gag gct      864
Gly Thr Tyr Glu Asn Gly Cys Ala His Val Asn Arg Leu Lys Glu Ala
        275                 280                 285 gaa gat cag aag gaa caa ata ggc acg gga tca cag aca gga atg tct      912
Glu Asp Gln Lys Glu Gln Ile Gly Thr Gly Ser Gln Thr Gly Met Ser
    290                 295                 300 atg agt aag aaa gct gaa gaa cca gga gat ctt gaa aag aat gca aag      960
Met Ser Lys Lys Ala Glu Glu Pro Gly Asp Leu Glu Lys Asn Ala Lys
305                 310                 315                 320 tat tct gtt caa gct ttg gag aga aac aat gat gac acg ctg aat cgc     1008
Tyr Ser Val Gln Ala Leu Glu Arg Asn Asn Asp Asp Thr Leu Asn Arg
                325                 330                 335 tct tct ggt aac tca caa gta gaa agc aaa gca cct tca tct aac cga     1056
Ser Ser Gly Asn Ser Gln Val Glu Ser Lys Ala Pro Ser Ser Asn Arg
            340                 345                 350 gaa gat ttg caa tca ctc gag caa act ctg aaa aaa aca aga gag gat     1104
Glu Asp Leu Gln Ser Leu Glu Gln Thr Leu Lys Lys Thr Arg Glu Asp
        355                 360                 365 aga gat tac aaa gtc ggt gat cga agt gtg ttg agg cat tca aat ctc     1152
Arg Asp Tyr Lys Val Gly Asp Arg Ser Val Leu Arg His Ser Asn Leu
    370                 375                 380 tct gca ttc tca aaa tac aat aat ggt gct act tct gct aag aag gct     1200
Ser Ala Phe Ser Lys Tyr Asn Asn Gly Ala Thr Ser Ala Lys Lys Ala
385                 390                 395                 400 cca gaa gaa aat gtg gaa agt tgt tct cct cat gac agt cct att gca     1248
Pro Glu Glu Asn Val Glu Ser Cys Ser Pro His Asp Ser Pro Ile Ala
                405                 410                 415 aaa ctg ttg ggt tcg agt tca agc agt gac aat cct tta aag cag cag     1296
Lys Leu Leu Gly Ser Ser Ser Ser Asp Asn Pro Leu Lys Gln Gln
            420                 425                 430 tct agt gga agt gac cga tgg gca caa aga gaa gct gct ttg atg aag     1344
Ser Ser Gly Ser Asp Arg Trp Ala Gln Arg Glu Ala Ala Leu Met Lys
        435                 440                 445 ttt cgc ctt aaa cgt aaa gag cga tgt ttt gag aaa aag gtt agg tac     1392
Phe Arg Leu Lys Arg Lys Glu Arg Cys Phe Glu Lys Lys Val Arg Tyr
```

-continued

```
                        450                 455                 460
cat agc agg aag aaa cta gct gag caa cgg cct cac gtc aaa ggt caa       1440
His Ser Arg Lys Lys Leu Ala Glu Gln Arg Pro His Val Lys Gly Gln
465                 470                 475                 480 ttc att cgc aag agg gat gat cat aaa tca gga agt gaa gac aat tga       1488
Phe Ile Arg Lys Arg Asp Asp His Lys Ser Gly Ser Glu Asp Asn
                485                 490                 495

<210> SEQ ID NO 4
<211> LENGTH: 495
<212> TYPE: PRT
<213> ORGANISM: Arabidopsis thaliana

<400> SEQUENCE: 4

Met Cys Phe Asn Asn Ile Glu Thr Gly Asp Glu Val Glu Thr Glu Arg
1               5                   10                  15

Gln Val Phe Gly Ser Ser Glu Glu Asp Glu Phe Arg Val Glu Asp Thr
                20                  25                  30

Ala Arg Asn Thr Asn Asn Val Gln Ile Ser Gln Gln Gln Gln Gln Pro
            35                  40                  45

Leu Ala His Val Val Lys Trp Glu Arg Tyr Leu Pro Val Arg Ser Leu
    50                  55                  60

Lys Val Leu Leu Val Glu Asn Asp Asp Ser Thr Arg His Ile Val Thr
65                  70                  75                  80

Ala Leu Leu Lys Asn Cys Ser Tyr Glu Val Thr Ala Val Pro Asp Val
                85                  90                  95

Leu Glu Ala Trp Arg Ile Leu Glu Asp Glu Lys Ser Cys Ile Asp Leu
            100                 105                 110

Val Leu Thr Glu Val Asp Met Pro Val His Ser Gly Thr Gly Leu Leu
        115                 120                 125

Ser Lys Ile Met Ser His Lys Thr Leu Lys Asn Ile Pro Val Ile Met
    130                 135                 140

Met Ser Ser His Asp Ser Met Val Leu Val Phe Lys Cys Leu Ser Asn
145                 150                 155                 160

Gly Ala Val Asp Phe Leu Val Lys Pro Ile Arg Lys Asn Glu Leu Lys
                165                 170                 175

Asn Leu Trp Gln His Val Trp Arg Arg Cys His Ser Ser Ser Gly Ser
            180                 185                 190

Gly Ser Glu Ser Gly Ile His Asp Lys Lys Ser Val Lys Pro Glu Ser
        195                 200                 205

Thr Gln Gly Ser Glu Asn Asp Ala Ser Ile Ser Asp Glu His Arg Asn
    210                 215                 220

Glu Ser Gly Ser Gly Gly Leu Ser Asn Gln Asp Gly Gly Ser Asp
225                 230                 235                 240

Asn Gly Ser Gly Thr Gln Ser Ser Trp Thr Lys Arg Ala Ser Asp Thr
                245                 250                 255

Lys Ser Thr Ser Pro Ser Asn Gln Phe Pro Asp Ala Pro Asn Lys Lys
            260                 265                 270

Gly Thr Tyr Glu Asn Gly Cys Ala His Val Asn Arg Leu Lys Glu Ala
        275                 280                 285

Glu Asp Gln Lys Glu Gln Ile Gly Thr Gly Ser Gln Thr Gly Met Ser
    290                 295                 300

Met Ser Lys Lys Ala Glu Glu Pro Gly Asp Leu Glu Lys Asn Ala Lys
305                 310                 315                 320

Tyr Ser Val Gln Ala Leu Glu Arg Asn Asn Asp Asp Thr Leu Asn Arg
```

```
                    325                 330                 335
Ser Ser Gly Asn Ser Gln Val Glu Ser Lys Ala Pro Ser Ser Asn Arg
            340                 345                 350

Glu Asp Leu Gln Ser Leu Glu Gln Thr Leu Lys Lys Thr Arg Glu Asp
        355                 360                 365

Arg Asp Tyr Lys Val Gly Asp Arg Ser Val Leu Arg His Ser Asn Leu
    370                 375                 380

Ser Ala Phe Ser Lys Tyr Asn Asn Gly Ala Thr Ser Ala Lys Lys Ala
385                 390                 395                 400

Pro Glu Glu Asn Val Glu Ser Cys Ser Pro His Asp Ser Pro Ile Ala
                405                 410                 415

Lys Leu Leu Gly Ser Ser Ser Ser Asp Asn Pro Leu Lys Gln Gln
                420                 425                 430

Ser Ser Gly Ser Asp Arg Trp Ala Gln Arg Glu Ala Ala Leu Met Lys
            435                 440                 445

Phe Arg Leu Lys Arg Lys Glu Arg Cys Phe Glu Lys Lys Val Arg Tyr
    450                 455                 460

His Ser Arg Lys Lys Leu Ala Glu Gln Arg Pro His Val Lys Gly Gln
465                 470                 475                 480

Phe Ile Arg Lys Arg Asp Asp His Lys Ser Gly Ser Glu Asp Asn
                485                 490                 495

<210> SEQ ID NO 5
<211> LENGTH: 1677
<212> TYPE: DNA
<213> ORGANISM: Arabidopsis thaliana
<220> FEATURE:
<221> NAME/KEY: CDS
<222> LOCATION: (1)..(1677)

<400> SEQUENCE: 5 atg act agt agc gag gaa gta gtt gaa gtg acg gtg gtt aaa gca cct      48
Met Thr Ser Ser Glu Glu Val Val Glu Val Thr Val Val Lys Ala Pro
1               5                   10                  15 gaa gct ggc gga gga aag tta tca cgt cgg aag att cgg aag aaa gac      96
Glu Ala Gly Gly Gly Lys Leu Ser Arg Arg Lys Ile Arg Lys Lys Asp
            20                  25                  30 gcc ggt gtt gat ggt ttg gtg aag tgg gag aga ttt ctc ccg aaa atc     144
Ala Gly Val Asp Gly Leu Val Lys Trp Glu Arg Phe Leu Pro Lys Ile
        35                  40                  45 gcg ctt aga gtt ttg ctc gtt gaa gct gat gat tct act aga cag att     192
Ala Leu Arg Val Leu Leu Val Glu Ala Asp Asp Ser Thr Arg Gln Ile
    50                  55                  60 atc gct gct ctt ctc agg aaa tgt agt tac aga gtt gct gca gta cct     240
Ile Ala Ala Leu Leu Arg Lys Cys Ser Tyr Arg Val Ala Ala Val Pro
65                  70                  75                  80 gat ggc tta aaa gct tgg gag atg cta aaa gga aag cct gaa agt gtt     288
Asp Gly Leu Lys Ala Trp Glu Met Leu Lys Gly Lys Pro Glu Ser Val
                85                  90                  95 gat ttg ata tta aca gag gtt gat cta cct tca ata tct gga tat gct     336
Asp Leu Ile Leu Thr Glu Val Asp Leu Pro Ser Ile Ser Gly Tyr Ala
            100                 105                 110 ctg cta aca ctt atc atg gag cat gat att tgc aag aac att cct gtt     384
Leu Leu Thr Leu Ile Met Glu His Asp Ile Cys Lys Asn Ile Pro Val
        115                 120                 125 ata atg atg tcg aca cag gac tcg gtg aat act gtg tat aag tgt atg     432
Ile Met Met Ser Thr Gln Asp Ser Val Asn Thr Val Tyr Lys Cys Met
    130                 135                 140
```

```
ttg aaa ggt gcg gct gat tat ctt gtt aag ccg ttg agg agg aat gag      480
Leu Lys Gly Ala Ala Asp Tyr Leu Val Lys Pro Leu Arg Arg Asn Glu
145                 150                 155                 160 ctt aga aat ctt tgg cag cat gtc tgg aga aga caa act tca ctt gct      528
Leu Arg Asn Leu Trp Gln His Val Trp Arg Arg Gln Thr Ser Leu Ala
                165                 170                 175 cct gat agc ttt cca tgg aat gag agt gtt gga cag cag aaa gcc gag      576
Pro Asp Ser Phe Pro Trp Asn Glu Ser Val Gly Gln Gln Lys Ala Glu
            180                 185                 190 ggt gcg tct gca aac aac tcg aac gga aag aga gac gat cat gtt gtg      624
Gly Ala Ser Ala Asn Asn Ser Asn Gly Lys Arg Asp Asp His Val Val
        195                 200                 205 agt ggg aat ggt ggt gat gcc cag agc tcg tgt aca aga cca gag atg      672
Ser Gly Asn Gly Gly Asp Ala Gln Ser Ser Cys Thr Arg Pro Glu Met
    210                 215                 220 gaa ggt gag agc gca gac gtg gag gtt agt gcg aga gac gca gta cag      720
Glu Gly Glu Ser Ala Asp Val Glu Val Ser Ala Arg Asp Ala Val Gln
225                 230                 235                 240 atg gag tgc gca aag tct cag ttt aat gag aca cgg ctt cta gca aat      768
Met Glu Cys Ala Lys Ser Gln Phe Asn Glu Thr Arg Leu Leu Ala Asn
                245                 250                 255 gag ttg cag agt aag caa gca gaa gcc att gac ttc atg gga gca tcg      816
Glu Leu Gln Ser Lys Gln Ala Glu Ala Ile Asp Phe Met Gly Ala Ser
            260                 265                 270 ttt aga aga act gga cga cgt aac aga gaa gaa agt gtt gct caa tac      864
Phe Arg Arg Thr Gly Arg Arg Asn Arg Glu Glu Ser Val Ala Gln Tyr
        275                 280                 285 gaa tct cgg ata gag ctt gat ctt tct ctg aga aga cct aat gct tct      912
Glu Ser Arg Ile Glu Leu Asp Leu Ser Leu Arg Arg Pro Asn Ala Ser
    290                 295                 300 gag aac caa tct tct gga gac cgg cct tct ctt cat cct tct agt gcc      960
Glu Asn Gln Ser Ser Gly Asp Arg Pro Ser Leu His Pro Ser Ser Ala
305                 310                 315                 320 tca gct ttc aca cgg tac gtt cac agg ccg ttg cag aca caa tgt tca     1008
Ser Ala Phe Thr Arg Tyr Val His Arg Pro Leu Gln Thr Gln Cys Ser
                325                 330                 335 gcc tcc cca gtg gtt act gat caa aga aag aat gtt gca gca agt caa     1056
Ala Ser Pro Val Val Thr Asp Gln Arg Lys Asn Val Ala Ala Ser Gln
            340                 345                 350 gat gat aac att gtg cta atg aac caa tac aat aca tct gaa ccg cct     1104
Asp Asp Asn Ile Val Leu Met Asn Gln Tyr Asn Thr Ser Glu Pro Pro
        355                 360                 365 cca aat gct cca aga aga aac gac acc agc ttt tac act gga gct gac     1152
Pro Asn Ala Pro Arg Arg Asn Asp Thr Ser Phe Tyr Thr Gly Ala Asp
    370                 375                 380 tca cct ggt cca ccg ttt agt aat cag ctg aat tct tgg ccg gga cag     1200
Ser Pro Gly Pro Pro Phe Ser Asn Gln Leu Asn Ser Trp Pro Gly Gln
385                 390                 395                 400 agt tca tac cct acg cca acc cct atc aac aat ata cag ttc aga gat     1248
Ser Ser Tyr Pro Thr Pro Thr Pro Ile Asn Asn Ile Gln Phe Arg Asp
                405                 410                 415 ccc aac aca gct tat aca tct gca atg gct cct gct tca ctc tcc cca     1296
Pro Asn Thr Ala Tyr Thr Ser Ala Met Ala Pro Ala Ser Leu Ser Pro
            420                 425                 430 agc cct agt tcc gtt agc ccg cat gag tac agt tcc atg ttt cac cca     1344
Ser Pro Ser Ser Val Ser Pro His Glu Tyr Ser Ser Met Phe His Pro
        435                 440                 445 ttc aac agt aaa ccc gag ggg tta caa gac cgg gat tgt tcc atg gat     1392
Phe Asn Ser Lys Pro Glu Gly Leu Gln Asp Arg Asp Cys Ser Met Asp
    450                 455                 460
```

```
gta gat gag agg aga tac gtc tct tct gca acc gaa cat agt gca ata    1440
Val Asp Glu Arg Arg Tyr Val Ser Ser Ala Thr Glu His Ser Ala Ile
465             470                 475                 480 ggc aat cac att gat cag ctt att gag aag aag aac gaa gat ggc tat    1488
Gly Asn His Ile Asp Gln Leu Ile Glu Lys Lys Asn Glu Asp Gly Tyr
                485                 490                 495 tca tta tcc gtc ggg aaa att cag caa tct ctt caa cga gaa gcc gct    1536
Ser Leu Ser Val Gly Lys Ile Gln Gln Ser Leu Gln Arg Glu Ala Ala
            500                 505                 510 tta acc aaa ttc cga atg aag cga aag gac aga tgt tat gag aaa aag    1584
Leu Thr Lys Phe Arg Met Lys Arg Lys Asp Arg Cys Tyr Glu Lys Lys
        515                 520                 525 gtt cgt tac gag agc cgg aag aaa tta gca gag caa cga cca cga atc    1632
Val Arg Tyr Glu Ser Arg Lys Lys Leu Ala Glu Gln Arg Pro Arg Ile
    530                 535                 540 aaa ggc caa ttc gtt cgt caa gtc caa tcc aca caa gct cca tag        1677
Lys Gly Gln Phe Val Arg Gln Val Gln Ser Thr Gln Ala Pro
545                 550                 555

<210> SEQ ID NO 6
<211> LENGTH: 558
<212> TYPE: PRT
<213> ORGANISM: Arabidopsis thaliana

<400> SEQUENCE: 6

Met Thr Ser Ser Glu Val Val Glu Val Thr Val Val Lys Ala Pro
1               5                   10                  15

Glu Ala Gly Gly Gly Lys Leu Ser Arg Arg Lys Ile Arg Lys Asp
            20                  25                  30

Ala Gly Val Asp Gly Leu Val Lys Trp Glu Arg Phe Leu Pro Lys Ile
            35                  40                  45

Ala Leu Arg Val Leu Val Glu Ala Asp Asp Ser Thr Arg Gln Ile
    50                  55                  60

Ile Ala Ala Leu Leu Arg Lys Cys Ser Tyr Arg Val Ala Ala Val Pro
65                  70                  75                  80

Asp Gly Leu Lys Ala Trp Glu Met Leu Lys Gly Lys Pro Glu Ser Val
                85                  90                  95

Asp Leu Ile Leu Thr Glu Val Asp Leu Pro Ser Ile Ser Gly Tyr Ala
            100                 105                 110

Leu Leu Thr Leu Ile Met Glu His Asp Ile Cys Lys Asn Ile Pro Val
            115                 120                 125

Ile Met Met Ser Thr Gln Asp Ser Val Asn Thr Val Tyr Lys Cys Met
    130                 135                 140

Leu Lys Gly Ala Ala Asp Tyr Leu Val Lys Pro Leu Arg Arg Asn Glu
145                 150                 155                 160

Leu Arg Asn Leu Trp Gln His Val Trp Arg Arg Gln Thr Ser Leu Ala
                165                 170                 175

Pro Asp Ser Phe Pro Trp Asn Glu Ser Val Gly Gln Gln Lys Ala Glu
            180                 185                 190

Gly Ala Ser Ala Asn Asn Ser Asn Gly Lys Arg Asp Asp His Val Val
        195                 200                 205

Ser Gly Asn Gly Gly Asp Ala Gln Ser Ser Cys Thr Arg Pro Glu Met
    210                 215                 220

Glu Gly Glu Ser Ala Asp Val Glu Val Ser Ala Arg Asp Ala Val Gln
225                 230                 235                 240

Met Glu Cys Ala Lys Ser Gln Phe Asn Glu Thr Arg Leu Leu Ala Asn
```

```
                  245                 250                 255
Glu Leu Gln Ser Lys Gln Ala Glu Ala Ile Asp Phe Met Gly Ala Ser
            260                 265                 270

Phe Arg Arg Thr Gly Arg Arg Asn Arg Glu Glu Ser Val Ala Gln Tyr
        275                 280                 285

Glu Ser Arg Ile Glu Leu Asp Leu Ser Leu Arg Arg Pro Asn Ala Ser
    290                 295                 300

Glu Asn Gln Ser Ser Gly Asp Arg Pro Ser Leu His Pro Ser Ser Ala
305                 310                 315                 320

Ser Ala Phe Thr Arg Tyr Val His Arg Pro Leu Gln Thr Gln Cys Ser
                325                 330                 335

Ala Ser Pro Val Val Thr Asp Gln Arg Lys Asn Val Ala Ala Ser Gln
            340                 345                 350

Asp Asp Asn Ile Val Leu Met Asn Gln Tyr Asn Thr Ser Glu Pro Pro
        355                 360                 365

Pro Asn Ala Pro Arg Arg Asn Asp Thr Ser Phe Tyr Thr Gly Ala Asp
    370                 375                 380

Ser Pro Gly Pro Pro Phe Ser Asn Gln Leu Asn Ser Trp Pro Gly Gln
385                 390                 395                 400

Ser Ser Tyr Pro Thr Pro Thr Pro Ile Asn Asn Ile Gln Phe Arg Asp
                405                 410                 415

Pro Asn Thr Ala Tyr Thr Ser Ala Met Ala Pro Ala Ser Leu Ser Pro
            420                 425                 430

Ser Pro Ser Ser Val Ser Pro His Glu Tyr Ser Ser Met Phe His Pro
        435                 440                 445

Phe Asn Ser Lys Pro Glu Gly Leu Gln Asp Arg Asp Cys Ser Met Asp
    450                 455                 460

Val Asp Glu Arg Arg Tyr Val Ser Ser Ala Thr Glu His Ser Ala Ile
465                 470                 475                 480

Gly Asn His Ile Asp Gln Leu Ile Glu Lys Lys Asn Glu Asp Gly Tyr
                485                 490                 495

Ser Leu Ser Val Gly Lys Ile Gln Gln Ser Leu Gln Arg Glu Ala Ala
            500                 505                 510

Leu Thr Lys Phe Arg Met Lys Arg Lys Asp Arg Cys Tyr Glu Lys Lys
        515                 520                 525

Val Arg Tyr Glu Ser Arg Lys Lys Leu Ala Glu Gln Arg Pro Arg Ile
    530                 535                 540

Lys Gly Gln Phe Val Arg Gln Val Gln Ser Thr Gln Ala Pro
545                 550                 555

<210> SEQ ID NO 7
<211> LENGTH: 2184
<212> TYPE: DNA
<213> ORGANISM: Arabidopsis thaliana
<220> FEATURE:
<221> NAME/KEY: CDS
<222> LOCATION: (1)..(2184)

<400> SEQUENCE: 7 atg aat gct aat gag gag ggg gag ggt tca cgt tac cca atc act gat      48
Met Asn Ala Asn Glu Glu Gly Glu Gly Ser Arg Tyr Pro Ile Thr Asp
1               5                   10                  15 cga aag acc gga gag acg aaa ttc gat agg gtt gag agt cgg aca gag      96
Arg Lys Thr Gly Glu Thr Lys Phe Asp Arg Val Glu Ser Arg Thr Glu
            20                  25                  30 aag cat agt gaa gaa gag aaa act aat gga att act atg gat gtg aga     144
```

```
                Lys His Ser Glu Glu Lys Thr Asn Gly Ile Thr Met Asp Val Arg
                        35                  40                  45 aat ggg agt tca ggt gga ctg caa att cca ttg tcg caa caa aca gcg       192
Asn Gly Ser Ser Gly Gly Leu Gln Ile Pro Leu Ser Gln Gln Thr Ala
        50                  55                  60 gca act gtc tgt tgg gaa agg ttt ctt cat gtg aga acc att aga gtt       240
Ala Thr Val Cys Trp Glu Arg Phe Leu His Val Arg Thr Ile Arg Val
65                  70                  75                  80 ctg ctt gtc gaa aat gac gac tgc act cgt tat atc gtt act gca ctt       288
Leu Leu Val Glu Asn Asp Asp Cys Thr Arg Tyr Ile Val Thr Ala Leu
                85                  90                  95 ctt cgc aat tgt agc tat gaa gtt gtt gag gcg tca aat ggg ata caa       336
Leu Arg Asn Cys Ser Tyr Glu Val Val Glu Ala Ser Asn Gly Ile Gln
            100                 105                 110 gct tgg aag gtg tta gaa gat cta aac aat cat att gat att gtg cta       384
Ala Trp Lys Val Leu Glu Asp Leu Asn Asn His Ile Asp Ile Val Leu
        115                 120                 125 aca gag gtg atc atg cct tac tta tct ggt atc ggt ctc ttg tgc aag       432
Thr Glu Val Ile Met Pro Tyr Leu Ser Gly Ile Gly Leu Leu Cys Lys
    130                 135                 140 att ttg aac cac aaa tct cgt cgg aac atc cct gtc atc atg atg tca       480
Ile Leu Asn His Lys Ser Arg Arg Asn Ile Pro Val Ile Met Met Ser
145                 150                 155                 160 tct cat gac tca atg ggg ctg gtc ttt aag tgc tta tcg aaa gga gct       528
Ser His Asp Ser Met Gly Leu Val Phe Lys Cys Leu Ser Lys Gly Ala
                165                 170                 175 gtt gac ttt ctt gtt aag cca ata aga aaa aat gag ctt aag atc ctt       576
Val Asp Phe Leu Val Lys Pro Ile Arg Lys Asn Glu Leu Lys Ile Leu
            180                 185                 190 tgg cag cat gtt tgg aga aga tgc caa agt tct agt ggt agt gga agt       624
Trp Gln His Val Trp Arg Arg Cys Gln Ser Ser Ser Gly Ser Gly Ser
        195                 200                 205 gag agc gga acg cat caa act caa aag tct gtg aaa tcg aaa agt att       672
Glu Ser Gly Thr His Gln Thr Gln Lys Ser Val Lys Ser Lys Ser Ile
    210                 215                 220 aaa aaa tct gat caa gat tca gga agc agt gat gag aat gaa aat ggg       720
Lys Lys Ser Asp Gln Asp Ser Gly Ser Ser Asp Glu Asn Glu Asn Gly
225                 230                 235                 240 agc att ggc ctg aat gct agt gat gga agt agt gat ggg agt ggc gct       768
Ser Ile Gly Leu Asn Ala Ser Asp Gly Ser Ser Asp Gly Ser Gly Ala
                245                 250                 255 cag agc tct tgg acg aaa aaa gct gtg gat gtt gat gac agt cca cga       816
Gln Ser Ser Trp Thr Lys Lys Ala Val Asp Val Asp Asp Ser Pro Arg
            260                 265                 270 gcg gta tct cta tgg gac cga gtt gat agc act tgc gcc caa gtg gta       864
Ala Val Ser Leu Trp Asp Arg Val Asp Ser Thr Cys Ala Gln Val Val
        275                 280                 285 cat tct aac cct gag ttt cca agt aat cag ttg gtt gca cca cct gct       912
His Ser Asn Pro Glu Phe Pro Ser Asn Gln Leu Val Ala Pro Pro Ala
    290                 295                 300 gag aag gag act caa gaa cat gat gat aaa ttt gaa gat gtc aca atg       960
Glu Lys Glu Thr Gln Glu His Asp Asp Lys Phe Glu Asp Val Thr Met
305                 310                 315                 320 ggt aga gac ttg gag att agc att cgt aga aac tgt gat ctg gcc ctg      1008
Gly Arg Asp Leu Glu Ile Ser Ile Arg Arg Asn Cys Asp Leu Ala Leu
                325                 330                 335 gag cca aaa gat gaa ccc cta tct aaa act act ggc att atg aga cag      1056
Glu Pro Lys Asp Glu Pro Leu Ser Lys Thr Thr Gly Ile Met Arg Gln
            340                 345                 350
```

```
gat aat tcg ttt gaa aag agc tct agt aaa tgg aaa atg aaa gtt gga    1104
Asp Asn Ser Phe Glu Lys Ser Ser Ser Lys Trp Lys Met Lys Val Gly
            355                 360                 365 aaa gga cca ttg gac ctc agt agc gaa agt cct tca agt aaa caa atg    1152
Lys Gly Pro Leu Asp Leu Ser Ser Glu Ser Pro Ser Ser Lys Gln Met
370                 375                 380 cat gaa gat gga ggc tcg agt ttc aaa gct atg tct agc cac ctt caa    1200
His Glu Asp Gly Gly Ser Ser Phe Lys Ala Met Ser Ser His Leu Gln
385                 390                 395                 400 gat aac aga gaa cct gag gcg cct aac act cac ttg aaa act tta gat    1248
Asp Asn Arg Glu Pro Glu Ala Pro Asn Thr His Leu Lys Thr Leu Asp
                405                 410                 415 aca aat gaa gct tct gtt aaa att tct gaa gag cta atg cac gtg gaa    1296
Thr Asn Glu Ala Ser Val Lys Ile Ser Glu Glu Leu Met His Val Glu
            420                 425                 430 cat agt tca aag agg cat aga gga act aaa gat gat ggg aca cta gtt    1344
His Ser Ser Lys Arg His Arg Gly Thr Lys Asp Asp Gly Thr Leu Val
            435                 440                 445 agg gat gat cgg aat gtg ctg agg cgt tca gag ggc tca gct ttc tca    1392
Arg Asp Asp Arg Asn Val Leu Arg Arg Ser Glu Gly Ser Ala Phe Ser
450                 455                 460 agg tat aat cca gcc tca aat gcc aat aag att tct ggt ggg aac tta    1440
Arg Tyr Asn Pro Ala Ser Asn Ala Asn Lys Ile Ser Gly Gly Asn Leu
465                 470                 475                 480 gga agc act tcg ctt cag gat aat aat agt cag gat ctt ata aaa aag    1488
Gly Ser Thr Ser Leu Gln Asp Asn Asn Ser Gln Asp Leu Ile Lys Lys
            485                 490                 495 act gaa gca gca tat gat tgt cac tcg aac atg aat gag agt ctc ccc    1536
Thr Glu Ala Ala Tyr Asp Cys His Ser Asn Met Asn Glu Ser Leu Pro
            500                 505                 510 cat aat cat cgc tca cat gtc ggt agc aat aac ttt gat atg agt tcc    1584
His Asn His Arg Ser His Val Gly Ser Asn Asn Phe Asp Met Ser Ser
            515                 520                 525 acg act gag aac aac gct ttc aca aaa cca gga gct cca aaa gta agc    1632
Thr Thr Glu Asn Asn Ala Phe Thr Lys Pro Gly Ala Pro Lys Val Ser
530                 535                 540 tca gca gga tct tca tca gtg aag cat tca tcg ttt cag cct tta ccc    1680
Ser Ala Gly Ser Ser Ser Val Lys His Ser Ser Phe Gln Pro Leu Pro
545                 550                 555                 560 tgt gat cat cat aat aat cat gcc tcc tat aac ctt gtc cat gtc gct    1728
Cys Asp His His Asn Asn His Ala Ser Tyr Asn Leu Val His Val Ala
            565                 570                 575 gag agg aag aag cta ccg cca caa tgt gga tcc tca aat gtg tac aac    1776
Glu Arg Lys Lys Leu Pro Pro Gln Cys Gly Ser Ser Asn Val Tyr Asn
            580                 585                 590 gaa acg att gaa ggt aac aac aac aca gtg aat tac agt gtg aat gga    1824
Glu Thr Ile Glu Gly Asn Asn Asn Thr Val Asn Tyr Ser Val Asn Gly
            595                 600                 605 agt gta tca ggt agt ggt cat gga agt aat ggg cca tat gga agc agt    1872
Ser Val Ser Gly Ser Gly His Gly Ser Asn Gly Pro Tyr Gly Ser Ser
610                 615                 620 aac ggt atg aat gct gga gga atg aat atg gga agt gat aat ggt gct    1920
Asn Gly Met Asn Ala Gly Gly Met Asn Met Gly Ser Asp Asn Gly Ala
625                 630                 635                 640 ggc aaa aat gga aat ggc gat ggt agt gga agc gga agt gga agt ggt    1968
Gly Lys Asn Gly Asn Gly Asp Gly Ser Gly Ser Gly Ser Gly Ser Gly
                645                 650                 655 agc gga aac ttg gcg gat gaa aat aag atc tct caa agg gaa gct gct    2016
Ser Gly Asn Leu Ala Asp Glu Asn Lys Ile Ser Gln Arg Glu Ala Ala
            660                 665                 670
```

```
ttg aca aag ttc cgt cag aag aga aaa gag agg tgc ttc cga aag aag    2064
Leu Thr Lys Phe Arg Gln Lys Arg Lys Glu Arg Cys Phe Arg Lys Lys
        675                 680                 685 gta cga tac caa agc cgg aaa aaa cta gca gaa caa cgc cct cga gtg    2112
Val Arg Tyr Gln Ser Arg Lys Lys Leu Ala Glu Gln Arg Pro Arg Val
        690                 695                 700 cga ggc caa ttt gtg cgt aaa aca gcc gct gca act gat gat aac gac    2160
Arg Gly Gln Phe Val Arg Lys Thr Ala Ala Ala Thr Asp Asp Asn Asp
705                 710                 715                 720 ata aaa aac att gag gat agc taa                                    2184
Ile Lys Asn Ile Glu Asp Ser
                725

<210> SEQ ID NO 8
<211> LENGTH: 727
<212> TYPE: PRT
<213> ORGANISM: Arabidopsis thaliana

<400> SEQUENCE: 8

Met Asn Ala Asn Glu Glu Gly Glu Gly Ser Arg Tyr Pro Ile Thr Asp
1               5                   10                  15

Arg Lys Thr Gly Glu Thr Lys Phe Asp Arg Val Glu Ser Arg Thr Glu
            20                  25                  30

Lys His Ser Glu Glu Lys Thr Asn Gly Ile Thr Met Asp Val Arg
        35                  40                  45

Asn Gly Ser Ser Gly Gly Leu Gln Ile Pro Leu Ser Gln Gln Thr Ala
    50                  55                  60

Ala Thr Val Cys Trp Glu Arg Phe Leu His Val Arg Thr Ile Arg Val
65                  70                  75                  80

Leu Leu Val Glu Asn Asp Asp Cys Thr Arg Tyr Ile Val Thr Ala Leu
                85                  90                  95

Leu Arg Asn Cys Ser Tyr Glu Val Val Glu Ala Ser Asn Gly Ile Gln
            100                 105                 110

Ala Trp Lys Val Leu Glu Asp Leu Asn Asn His Ile Asp Ile Val Leu
        115                 120                 125

Thr Glu Val Ile Met Pro Tyr Leu Ser Gly Ile Gly Leu Leu Cys Lys
    130                 135                 140

Ile Leu Asn His Lys Ser Arg Arg Asn Ile Pro Val Ile Met Met Ser
145                 150                 155                 160

Ser His Asp Ser Met Gly Leu Val Phe Lys Cys Leu Ser Lys Gly Ala
                165                 170                 175

Val Asp Phe Leu Val Lys Pro Ile Arg Lys Asn Glu Leu Lys Ile Leu
            180                 185                 190

Trp Gln His Val Trp Arg Arg Cys Gln Ser Ser Gly Ser Gly Ser
        195                 200                 205

Glu Ser Gly Thr His Gln Thr Gln Lys Ser Val Lys Ser Lys Ser Ile
    210                 215                 220

Lys Lys Ser Asp Gln Asp Ser Gly Ser Ser Asp Glu Asn Glu Asn Gly
225                 230                 235                 240

Ser Ile Gly Leu Asn Ala Ser Asp Gly Ser Ser Asp Gly Ser Gly Ala
                245                 250                 255

Gln Ser Ser Trp Thr Lys Lys Ala Val Asp Val Asp Asp Ser Pro Arg
            260                 265                 270

Ala Val Ser Leu Trp Asp Arg Val Asp Ser Thr Cys Ala Gln Val Val
        275                 280                 285
```

-continued

```
His Ser Asn Pro Glu Phe Pro Ser Asn Gln Leu Val Ala Pro Pro Ala
    290             295             300
Glu Lys Glu Thr Gln Glu His Asp Asp Lys Phe Glu Asp Val Thr Met
305             310             315                 320
Gly Arg Asp Leu Glu Ile Ser Ile Arg Arg Asn Cys Asp Leu Ala Leu
                325             330             335
Glu Pro Lys Asp Glu Pro Leu Ser Lys Thr Thr Gly Ile Met Arg Gln
            340             345             350
Asp Asn Ser Phe Glu Lys Ser Ser Lys Trp Lys Met Lys Val Gly
        355             360             365
Lys Gly Pro Leu Asp Leu Ser Ser Glu Ser Pro Ser Ser Lys Gln Met
370             375             380
His Glu Asp Gly Gly Ser Ser Phe Lys Ala Met Ser Ser His Leu Gln
385             390             395                 400
Asp Asn Arg Glu Pro Glu Ala Pro Asn Thr His Leu Lys Thr Leu Asp
                405             410             415
Thr Asn Glu Ala Ser Val Lys Ile Ser Glu Glu Leu Met His Val Glu
            420             425             430
His Ser Ser Lys Arg His Arg Gly Thr Lys Asp Asp Gly Thr Leu Val
        435             440             445
Arg Asp Asp Arg Asn Val Leu Arg Arg Ser Glu Gly Ser Ala Phe Ser
450             455             460
Arg Tyr Asn Pro Ala Ser Asn Ala Asn Lys Ile Ser Gly Gly Asn Leu
465             470             475                 480
Gly Ser Thr Ser Leu Gln Asp Asn Asn Ser Gln Asp Leu Ile Lys Lys
                485             490             495
Thr Glu Ala Ala Tyr Asp Cys His Ser Asn Met Asn Glu Ser Leu Pro
            500             505             510
His Asn His Arg Ser His Val Gly Ser Asn Asn Phe Asp Met Ser Ser
        515             520             525
Thr Thr Glu Asn Asn Ala Phe Thr Lys Pro Gly Ala Pro Lys Val Ser
530             535             540
Ser Ala Gly Ser Ser Ser Val Lys His Ser Ser Phe Gln Pro Leu Pro
545             550             555                 560
Cys Asp His His Asn Asn His Ala Ser Tyr Asn Leu Val His Val Ala
                565             570             575
Glu Arg Lys Lys Leu Pro Pro Gln Cys Gly Ser Ser Asn Val Tyr Asn
            580             585             590
Glu Thr Ile Glu Gly Asn Asn Asn Thr Val Asn Tyr Ser Val Asn Gly
        595             600             605
Ser Val Ser Gly Ser Gly His Gly Ser Asn Gly Pro Tyr Gly Ser Ser
610             615             620
Asn Gly Met Asn Ala Gly Gly Met Asn Met Gly Ser Asp Asn Gly Ala
625             630             635                 640
Gly Lys Asn Gly Asn Gly Asp Gly Ser Gly Ser Gly Ser Gly Ser Gly
                645             650             655
Ser Gly Asn Leu Ala Asp Glu Asn Lys Ile Ser Gln Arg Glu Ala Ala
            660             665             670
Leu Thr Lys Phe Arg Gln Lys Arg Lys Glu Arg Cys Phe Arg Lys Lys
        675             680             685
Val Arg Tyr Gln Ser Arg Lys Lys Leu Ala Glu Gln Arg Pro Arg Val
690             695             700
Arg Gly Gln Phe Val Arg Lys Thr Ala Ala Ala Thr Asp Asp Asn Asp
```

```
                705                 710                 715                 720
Ile Lys Asn Ile Glu Asp Ser
                725

<210> SEQ ID NO 9
<211> LENGTH: 1407
<212> TYPE: DNA
<213> ORGANISM: Arabidopsis thaliana
<220> FEATURE:
<221> NAME/KEY: CDS
<222> LOCATION: (1)..(1407)

<400> SEQUENCE: 9 atg ggg gag att gtg gtt tta agt agt gat gat ggt atg gag act ata      48
Met Gly Glu Ile Val Val Leu Ser Ser Asp Asp Gly Met Glu Thr Ile
1               5                   10                  15 aag aac aga gta aag tca tcg gaa gtt gtt cag tgg gag aag tat ttg      96
Lys Asn Arg Val Lys Ser Ser Glu Val Val Gln Trp Glu Lys Tyr Leu
            20                  25                  30 cct aaa act gta ctt agg gtt ttg tta gtt gaa tct gat tac tca act     144
Pro Lys Thr Val Leu Arg Val Leu Leu Val Glu Ser Asp Tyr Ser Thr
        35                  40                  45 cgt caa atc atc act gcc ctt ctt cgt aaa tgc tgt tac aaa gtt gta     192
Arg Gln Ile Ile Thr Ala Leu Leu Arg Lys Cys Cys Tyr Lys Val Val
    50                  55                  60 gct gtt tct gat ggt tta gct gcg tgg gag gtt cta aag gag aag tca     240
Ala Val Ser Asp Gly Leu Ala Ala Trp Glu Val Leu Lys Glu Lys Ser
65                  70                  75                  80 cat aac att gat ctt ata cta aca gag ctg gat ttg cca tct ata tct     288
His Asn Ile Asp Leu Ile Leu Thr Glu Leu Asp Leu Pro Ser Ile Ser
                85                  90                  95 ggt ttt gct ctg ctt gct ttg gta atg gag cat gaa gct tgc aag aac     336
Gly Phe Ala Leu Leu Ala Leu Val Met Glu His Glu Ala Cys Lys Asn
            100                 105                 110 att cct gtc ata atg atg tct tct caa gat tcg ata aaa atg gtg ttg     384
Ile Pro Val Ile Met Met Ser Ser Gln Asp Ser Ile Lys Met Val Leu
        115                 120                 125 aag tgt atg ctg aga ggt gct gct gat tat cta atc aaa cca atg agg     432
Lys Cys Met Leu Arg Gly Ala Ala Asp Tyr Leu Ile Lys Pro Met Arg
    130                 135                 140 aaa aac gag ttg aaa aat cta tgg caa cat gtt tgg aga aga ctg act     480
Lys Asn Glu Leu Lys Asn Leu Trp Gln His Val Trp Arg Arg Leu Thr
145                 150                 155                 160 ttg cgt gat gat cct act gct cat gct caa agc tta cca gct tca cag     528
Leu Arg Asp Asp Pro Thr Ala His Ala Gln Ser Leu Pro Ala Ser Gln
                165                 170                 175 cac aac ctt gaa gat act gat gaa act tgt gaa gat tcc aga tat cat     576
His Asn Leu Glu Asp Thr Asp Glu Thr Cys Glu Asp Ser Arg Tyr His
            180                 185                 190 tca gat caa gga agt ggt gct cag gct atc aat tac aat ggt cac aat     624
Ser Asp Gln Gly Ser Gly Ala Gln Ala Ile Asn Tyr Asn Gly His Asn
        195                 200                 205 aag ctg atg gag aat ggc aaa tca gtg gat gaa aga gac gag ttt aag     672
Lys Leu Met Glu Asn Gly Lys Ser Val Asp Glu Arg Asp Glu Phe Lys
    210                 215                 220 gaa act ttt gat gtg aca atg gat ttg att ggt gga att gac aag cgt     720
Glu Thr Phe Asp Val Thr Met Asp Leu Ile Gly Gly Ile Asp Lys Arg
225                 230                 235                 240 cct gat agt att tat aaa gac aag agt cga gat gag tgt gtt ggt cct     768
Pro Asp Ser Ile Tyr Lys Asp Lys Ser Arg Asp Glu Cys Val Gly Pro
                245                 250                 255
```

```
gag ctt gga ctt tct ctg aaa aga tct tgc tct gta agt ttt gag aac     816
Glu Leu Gly Leu Ser Leu Lys Arg Ser Cys Ser Val Ser Phe Glu Asn
        260                 265                 270 caa gat gaa agc aag cat caa aag ctt agc ctc tct gat gcg tcg gcc     864
Gln Asp Glu Ser Lys His Gln Lys Leu Ser Leu Ser Asp Ala Ser Ala
275                 280                 285 ttc tca aga ttt gag gaa agc aag tca gca gaa aaa gcc gtc gtt gct     912
Phe Ser Arg Phe Glu Glu Ser Lys Ser Ala Glu Lys Ala Val Val Ala
        290                 295                 300 tta gag gag agt act tca ggt gag cca aag aca cca acc gaa tca cat     960
Leu Glu Glu Ser Thr Ser Gly Glu Pro Lys Thr Pro Thr Glu Ser His
305                 310                 315                 320 gaa aag tta aga aaa gta aca tct gat caa gga agc gcc aca acg agc    1008
Glu Lys Leu Arg Lys Val Thr Ser Asp Gln Gly Ser Ala Thr Thr Ser
                325                 330                 335 agc aac cag gag aat atc gga tca tca agc gta agc ttc cgt aac caa    1056
Ser Asn Gln Glu Asn Ile Gly Ser Ser Ser Val Ser Phe Arg Asn Gln
            340                 345                 350 gtt ctt cag tcc aca gta acg aat cag aag caa gat tca ccc ata ccg    1104
Val Leu Gln Ser Thr Val Thr Asn Gln Lys Gln Asp Ser Pro Ile Pro
        355                 360                 365 gta gaa tca aat cgc gag aaa gca gct agc aag gaa gta gaa gct ggt    1152
Val Glu Ser Asn Arg Glu Lys Ala Ala Ser Lys Glu Val Glu Ala Gly
370                 375                 380 tct caa agc acc aat gag ggg att gct gga caa agc agt agc aca gag    1200
Ser Gln Ser Thr Asn Glu Gly Ile Ala Gly Gln Ser Ser Ser Thr Glu
385                 390                 395                 400 aaa cca aag gaa gaa gaa agt gcg aaa caa cgt tgg agt aga agc cag    1248
Lys Pro Lys Glu Glu Glu Ser Ala Lys Gln Arg Trp Ser Arg Ser Gln
                405                 410                 415 aga gaa gct gca ttg atg aag ttc cgg ttg aag agg aaa gat cga tgc    1296
Arg Glu Ala Ala Leu Met Lys Phe Arg Leu Lys Arg Lys Asp Arg Cys
            420                 425                 430 ttt gac aaa aag gtt cgg tac cag agc agg aag aag cta gca gaa caa    1344
Phe Asp Lys Lys Val Arg Tyr Gln Ser Arg Lys Lys Leu Ala Glu Gln
        435                 440                 445 cgt cct cga gtg aaa ggc cag ttc gtg cga acc gtg aat tca gac gcg    1392
Arg Pro Arg Val Lys Gly Gln Phe Val Arg Thr Val Asn Ser Asp Ala
450                 455                 460 tct aca aaa tca tga                                                 1407
Ser Thr Lys Ser
465

<210> SEQ ID NO 10
<211> LENGTH: 468
<212> TYPE: PRT
<213> ORGANISM: Arabidopsis thaliana

<400> SEQUENCE: 10

Met Gly Glu Ile Val Val Leu Ser Ser Asp Gly Met Glu Thr Ile
1               5                   10                  15

Lys Asn Arg Val Lys Ser Ser Glu Val Val Gln Trp Glu Lys Tyr Leu
                20                  25                  30

Pro Lys Thr Val Leu Arg Val Leu Val Glu Ser Asp Tyr Ser Thr
            35                  40                  45

Arg Gln Ile Ile Thr Ala Leu Leu Arg Lys Cys Cys Tyr Lys Val Val
        50                  55                  60

Ala Val Ser Asp Gly Leu Ala Ala Trp Glu Val Leu Lys Glu Lys Ser
65                  70                  75                  80
```

His Asn Ile Asp Leu Ile Leu Thr Glu Leu Asp Leu Pro Ser Ile Ser
            85                  90                  95

Gly Phe Ala Leu Leu Ala Leu Val Met Glu His Glu Ala Cys Lys Asn
            100                 105                 110

Ile Pro Val Ile Met Met Ser Ser Gln Asp Ser Ile Lys Met Val Leu
            115                 120                 125

Lys Cys Met Leu Arg Gly Ala Ala Asp Tyr Leu Ile Lys Pro Met Arg
130                 135                 140

Lys Asn Glu Leu Lys Asn Leu Trp Gln His Val Trp Arg Arg Leu Thr
145                 150                 155                 160

Leu Arg Asp Asp Pro Thr Ala His Ala Gln Ser Leu Pro Ala Ser Gln
                165                 170                 175

His Asn Leu Glu Asp Thr Asp Glu Thr Cys Glu Asp Ser Arg Tyr His
            180                 185                 190

Ser Asp Gln Gly Ser Gly Ala Gln Ala Ile Asn Tyr Asn Gly His Asn
            195                 200                 205

Lys Leu Met Glu Asn Gly Lys Ser Val Asp Glu Arg Asp Glu Phe Lys
            210                 215                 220

Glu Thr Phe Asp Val Thr Met Asp Leu Ile Gly Gly Ile Asp Lys Arg
225                 230                 235                 240

Pro Asp Ser Ile Tyr Lys Asp Lys Ser Arg Asp Glu Cys Val Gly Pro
                245                 250                 255

Glu Leu Gly Leu Ser Leu Lys Arg Ser Cys Ser Val Ser Phe Glu Asn
            260                 265                 270

Gln Asp Glu Ser Lys His Gln Lys Leu Ser Leu Ser Asp Ala Ser Ala
            275                 280                 285

Phe Ser Arg Phe Glu Glu Ser Lys Ser Ala Lys Ala Val Val Ala
            290                 295                 300

Leu Glu Glu Ser Thr Ser Gly Glu Pro Lys Thr Pro Thr Glu Ser His
305                 310                 315                 320

Glu Lys Leu Arg Lys Val Thr Ser Asp Gln Gly Ser Ala Thr Thr Ser
                325                 330                 335

Ser Asn Gln Glu Asn Ile Gly Ser Ser Ser Val Ser Phe Arg Asn Gln
            340                 345                 350

Val Leu Gln Ser Thr Val Thr Asn Gln Lys Gln Asp Ser Pro Ile Pro
            355                 360                 365

Val Glu Ser Asn Arg Glu Lys Ala Ala Ser Lys Glu Val Glu Ala Gly
            370                 375                 380

Ser Gln Ser Thr Asn Glu Gly Ile Ala Gly Gln Ser Ser Ser Thr Glu
385                 390                 395                 400

Lys Pro Lys Glu Glu Ser Ala Lys Gln Arg Trp Ser Arg Ser Gln
                405                 410                 415

Arg Glu Ala Ala Leu Met Lys Phe Arg Leu Lys Arg Lys Asp Arg Cys
            420                 425                 430

Phe Asp Lys Lys Val Arg Tyr Gln Ser Arg Lys Lys Leu Ala Glu Gln
            435                 440                 445

Arg Pro Arg Val Lys Gly Gln Phe Val Arg Thr Val Asn Ser Asp Ala
450                 455                 460

Ser Thr Lys Ser
465

<210> SEQ ID NO 11
<211> LENGTH: 237

<212> TYPE: DNA
<213> ORGANISM: Herpesvirus

<400> SEQUENCE: 11

```
gcccccccga ccgatgtcag cctgggggac gagctccact tagacggcga ggacgtggcg      60
atggcgcatg ccgacgcgct agacgatttc gatctggaca tgttggggga cggggattcc     120
ccgggtccgg gatttacccc ccacgactcc gccccctacg gcgctctgga tatggccgac     180
ttcgagtttg agcagatgtt taccgatgcc cttggaattg acgagtacgg tgggtag        237
```

<210> SEQ ID NO 12
<211> LENGTH: 134
<212> TYPE: PRT
<213> ORGANISM: Arabidopsis thaliana

<400> SEQUENCE: 12

```
Phe Ile Asp Arg Ser Arg Val Arg Ile Leu Leu Cys Asp Asn Asp Ser
1               5                   10                  15

Thr Ser Leu Gly Glu Val Phe Thr Leu Ser Glu Cys Ser Tyr Gln
            20                  25                  30

Val Thr Ala Val Lys Ser Ala Arg Gln Val Ile Asp Ala Leu Asn Ala
        35                  40                  45

Glu Gly Pro Asp Ile Asp Ile Leu Ala Glu Ile Asp Leu Pro Met
    50                  55                  60

Ala Lys Gly Met Lys Met Leu Arg Tyr Ile Thr Arg Asp Lys Asp Leu
65                  70                  75                  80

Arg Arg Ile Pro Val Ile Met Met Ser Arg Gln Asp Glu Val Pro Val
                85                  90                  95

Val Val Lys Cys Leu Lys Leu Gly Ala Ala Asp Tyr Leu Val Lys Pro
            100                 105                 110

Leu Arg Thr Asn Glu Leu Leu Asn Leu Trp Thr His Met Trp Arg Arg
        115                 120                 125

Arg Arg Met Leu Gly Leu
    130
```

<210> SEQ ID NO 13
<211> LENGTH: 132
<212> TYPE: PRT
<213> ORGANISM: Arabidopsis thaliana

<400> SEQUENCE: 13

```
Lys Trp Glu Arg Tyr Leu Pro Val Arg Ser Leu Lys Val Leu Leu Val
1               5                   10                  15

Glu Asn Asp Asp Ser Thr Arg His Ile Val Thr Ala Leu Leu Lys Asn
            20                  25                  30

Cys Ser Tyr Glu Val Thr Ala Val Pro Asp Val Leu Glu Ala Trp Arg
        35                  40                  45

Ile Leu Glu Asp Glu Lys Ser Cys Ile Asp Leu Val Leu Thr Glu Val
    50                  55                  60

Asp Met Pro Val His Ser Gly Thr Gly Leu Leu Ser Lys Ile Met Ser
65                  70                  75                  80

His Lys Thr Leu Lys Asn Ile Pro Val Ile Met Met Ser Ser His Asp
                85                  90                  95

Ser Met Val Leu Val Phe Lys Cys Leu Ser Asn Gly Ala Val Asp Phe
            100                 105                 110

Leu Val Lys Pro Ile Arg Lys Asn Glu Leu Lys Asn Leu Trp Gln His
        115                 120                 125
```

```
<210> SEQ ID NO 14
<211> LENGTH: 132
<212> TYPE: PRT
<213> ORGANISM: Arabidopsis thaliana

<400> SEQUENCE: 14

Lys Trp Glu Arg Phe Leu Pro Lys Ile Ala Leu Arg Val Leu Leu Val
  1               5                  10                  15

Glu Ala Asp Asp Ser Thr Arg Gln Ile Ile Ala Ala Leu Leu Arg Lys
             20                  25                  30

Cys Ser Tyr Arg Val Ala Ala Val Pro Asp Gly Leu Lys Ala Trp Glu
         35                  40                  45

Met Leu Lys Gly Lys Pro Glu Ser Val Asp Leu Ile Leu Thr Glu Val
     50                  55                  60

Asp Leu Pro Ser Ile Ser Gly Tyr Ala Leu Leu Thr Leu Ile Met Glu
 65                  70                  75                  80

His Asp Ile Cys Lys Asn Ile Pro Val Ile Met Met Ser Thr Gln Asp
                 85                  90                  95

Ser Val Asn Thr Val Tyr Lys Cys Met Leu Lys Gly Ala Ala Asp Tyr
            100                 105                 110

Leu Val Lys Pro Leu Arg Arg Asn Glu Leu Arg Asn Leu Trp Gln His
        115                 120                 125

Val Trp Arg Arg
    130

<210> SEQ ID NO 15
<211> LENGTH: 132
<212> TYPE: PRT
<213> ORGANISM: Arabidopsis thaliana

<400> SEQUENCE: 15

Cys Trp Glu Arg Phe Leu His Val Arg Thr Ile Arg Val Leu Leu Val
  1               5                  10                  15

Glu Asn Asp Asp Cys Thr Arg Tyr Ile Val Thr Ala Leu Leu Arg Asn
             20                  25                  30

Cys Ser Tyr Glu Val Val Glu Ala Ser Asn Gly Ile Gln Ala Trp Lys
         35                  40                  45

Val Leu Glu Asp Leu Asn Asn His Ile Asp Ile Val Leu Thr Glu Val
     50                  55                  60

Ile Met Pro Tyr Leu Ser Gly Ile Gly Leu Leu Cys Lys Ile Leu Asn
 65                  70                  75                  80

His Lys Ser Arg Arg Asn Ile Pro Val Ile Met Met Ser Ser His Asp
                 85                  90                  95

Ser Met Gly Leu Val Phe Lys Cys Leu Ser Lys Gly Ala Val Asp Phe
            100                 105                 110

Leu Val Lys Pro Ile Arg Lys Asn Glu Leu Lys Ile Leu Trp Gln His
        115                 120                 125

Val Trp Arg Arg
    130

<210> SEQ ID NO 16
<211> LENGTH: 132
<212> TYPE: PRT
<213> ORGANISM: Arabidopsis thaliana
```

<400> SEQUENCE: 16

Gln Trp Glu Lys Tyr Leu Pro Lys Thr Val Leu Arg Val Leu Val
1               5                   10                  15

Glu Ser Asp Tyr Ser Thr Arg Gln Ile Ile Thr Ala Leu Leu Arg Lys
            20                  25                  30

Cys Cys Tyr Lys Val Val Ala Val Ser Asp Gly Leu Ala Ala Trp Glu
        35                  40                  45

Val Leu Lys Glu Lys Ser His Asn Ile Asp Leu Ile Leu Thr Glu Leu
    50                  55                  60

Asp Leu Pro Ser Ile Ser Gly Phe Ala Leu Leu Ala Leu Val Met Glu
65                  70                  75                  80

His Glu Ala Cys Lys Asn Ile Pro Val Ile Met Met Ser Ser Gln Asp
                85                  90                  95

Ser Ile Lys Met Val Leu Lys Cys Met Leu Arg Gly Ala Ala Asp Tyr
            100                 105                 110

Leu Ile Lys Pro Met Arg Lys Asn Glu Leu Lys Asn Leu Trp Gln His
        115                 120                 125

Val Trp Arg Arg
    130

<210> SEQ ID NO 17
<211> LENGTH: 46
<212> TYPE: PRT
<213> ORGANISM: Arabidopsis thaliana

<400> SEQUENCE: 17

Arg Arg Glu Glu Ala Leu Leu Lys Phe Arg Arg Lys Arg Asn Gln Arg
1               5                   10                  15

Cys Phe Asp Lys Lys Ile Arg Tyr Val Asn Arg Lys Arg Leu Ala Glu
            20                  25                  30

Arg Arg Pro Arg Val Lys Gly Gln Phe Val Arg Lys Met Asn
        35                  40                  45

<210> SEQ ID NO 18
<211> LENGTH: 45
<212> TYPE: PRT
<213> ORGANISM: Arabidopsis thaliana

<400> SEQUENCE: 18

Arg Glu Ala Ala Leu Met Lys Phe Arg Leu Lys Arg Lys Glu Arg Cys
1               5                   10                  15

Phe Glu Lys Lys Val Arg Tyr His Ser Arg Lys Lys Leu Ala Glu Gln
            20                  25                  30

Arg Pro His Val Lys Gly Gln Phe Ile Arg Lys Arg Asp
        35                  40                  45

<210> SEQ ID NO 19
<211> LENGTH: 45
<212> TYPE: PRT
<213> ORGANISM: Arabidopsis thaliana

<400> SEQUENCE: 19

Arg Glu Ala Ala Leu Thr Lys Phe Arg Met Lys Arg Lys Asp Arg Cys
1               5                   10                  15

Tyr Glu Lys Lys Val Arg Tyr Glu Ser Arg Lys Lys Leu Ala Glu Gln
            20                  25                  30

Arg Pro Arg Ile Lys Gly Gln Phe Val Arg Gln Val Gln
        35                  40                  45

<210> SEQ ID NO 20
<211> LENGTH: 45
<212> TYPE: PRT
<213> ORGANISM: Arabidopsis thaliana

<400> SEQUENCE: 20

Arg Glu Ala Ala Leu Thr Lys Phe Arg Gln Lys Arg Lys Glu Arg Cys
1               5                   10                  15
Phe Arg Lys Lys Val Arg Tyr Gln Ser Arg Lys Lys Leu Ala Glu Gln
                20                  25                  30
Arg Pro Arg Val Arg Gly Gln Phe Val Arg Lys Thr Ala
            35                  40                  45

<210> SEQ ID NO 21
<211> LENGTH: 45
<212> TYPE: PRT
<213> ORGANISM: Arabidopsis thaliana

<400> SEQUENCE: 21

Arg Glu Ala Ala Leu Met Lys Phe Arg Leu Lys Arg Lys Asp Arg Cys
1               5                   10                  15
Phe Asp Lys Lys Val Arg Tyr Gln Ser Arg Lys Lys Leu Ala Glu Gln
                20                  25                  30
Arg Pro Arg Val Lys Gly Gln Phe Val Arg Thr Val Asn
            35                  40                  45

<210> SEQ ID NO 22
<211> LENGTH: 8
<212> TYPE: PRT
<213> ORGANISM: Artificial
<220> FEATURE:
<223> OTHER INFORMATION: peptide

<400> SEQUENCE: 22

Asp Tyr Lys Asp Asp Asp Asp Lys
1               5

<210> SEQ ID NO 23
<211> LENGTH: 32
<212> TYPE: DNA
<213> ORGANISM: Artificial
<220> FEATURE:
<223> OTHER INFORMATION: primer

<400> SEQUENCE: 23
acactctaga atgactagta gcgaggaagt ag                                     32

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
gttggatcct ctggagcttg tgtggattgg                                        30

<210> SEQ ID NO 25
<211> LENGTH: 30
<212> TYPE: DNA
<213> ORGANISM: Artificial
<220> FEATURE:

```
<223> OTHER INFORMATION: primer

<400> SEQUENCE: 25
cttatctaga atgaatgcta atgaggaggg                                    30

<210> SEQ ID NO 26
<211> LENGTH: 35
<212> TYPE: DNA
<213> ORGANISM: Artificial
<220> FEATURE:
<223> OTHER INFORMATION: primer

<400> SEQUENCE: 26
gagtccatgg tgctatcctc aatgttttt atgtc                              35

<210> SEQ ID NO 27
<211> LENGTH: 26
<212> TYPE: DNA
<213> ORGANISM: Artificial
<220> FEATURE:
<223> OTHER INFORMATION: primer

<400> SEQUENCE: 27
caaatctaga atgggggaga ttgtgg                                        26

<210> SEQ ID NO 28
<211> LENGTH: 32
<212> TYPE: DNA
<213> ORGANISM: Artificial
<220> FEATURE:
<223> OTHER INFORMATION: primer

<400> SEQUENCE: 28
gaagtccatg gttgattttg tagacgcgtc tg                                 32

<210> SEQ ID NO 29
<211> LENGTH: 28
<212> TYPE: DNA
<213> ORGANISM: Artificial
<220> FEATURE:
<223> OTHER INFORMATION: primer

<400> SEQUENCE: 29
gtttaccatg gtgaaagtcg cccccccg                                      28

<210> SEQ ID NO 30
<211> LENGTH: 34
<212> TYPE: DNA
<213> ORGANISM: Artificial
<220> FEATURE:
<223> OTHER INFORMATION: primer

<400> SEQUENCE: 30
ctttaagctt cgggaattcc ccaccgtact cgtc                               34

<210> SEQ ID NO 31
<211> LENGTH: 25
<212> TYPE: DNA
<213> ORGANISM: Artificial
<220> FEATURE:
<223> OTHER INFORMATION: primer

<400> SEQUENCE: 31
ctttaagctt aaagtcgccc cccg                                          25
```

```
<210> SEQ ID NO 32
<211> LENGTH: 42
<212> TYPE: DNA
<213> ORGANISM: Artificial
<220> FEATURE:
<223> OTHER INFORMATION: primer

<400> SEQUENCE: 32
cgagaaagcg gccgcttacg ggaattcccc accgtactcg tc              42

<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33
cttcatcctt ctagtgcc                                         18

<210> SEQ ID NO 34
<211> LENGTH: 18
<212> TYPE: DNA
<213> ORGANISM: Artificial
<220> FEATURE:
<223> OTHER INFORMATION: primer

<400> SEQUENCE: 34
gtcgtttctt cttggagc                                         18

<210> SEQ ID NO 35
<211> LENGTH: 36
<212> TYPE: DNA
<213> ORGANISM: Artificial
<220> FEATURE:
<223> OTHER INFORMATION: primer

<400> SEQUENCE: 35
acgccaagct aagcttctag tatgttgaca tatggc                     36

<210> SEQ ID NO 36
<211> LENGTH: 38
<212> TYPE: DNA
<213> ORGANISM: Artificial
<220> FEATURE:
<223> OTHER INFORMATION: primer

<400> SEQUENCE: 36
gaagggtctt gcgatatcgc tacggaaatg gagaaatc                   38

<210> SEQ ID NO 37
<211> LENGTH: 27
<212> TYPE: DNA
<213> ORGANISM: Artificial
<220> FEATURE:
<223> OTHER INFORMATION: primer

<400> SEQUENCE: 37
caccatgggg gagattgtgg ttttaag                               27

<210> SEQ ID NO 38
<211> LENGTH: 20
<212> TYPE: DNA
<213> ORGANISM: Artificial
<220> FEATURE:
<223> OTHER INFORMATION: primer
```

<400> SEQUENCE: 38
tgattttgta gacgcgtctg                                            20

<210> SEQ ID NO 39
<211> LENGTH: 24
<212> TYPE: DNA
<213> ORGANISM: Artificial
<220> FEATURE:
<223> OTHER INFORMATION: primer

<400> SEQUENCE: 39
caccatgaat gctaatgagg aggg                                       24

<210> SEQ ID NO 40
<211> LENGTH: 24
<212> TYPE: DNA
<213> ORGANISM: Artificial
<220> FEATURE:
<223> OTHER INFORMATION: primer

<400> SEQUENCE: 40
gctatcctca atgtttttta tgtc                                       24

<210> SEQ ID NO 41
<211> LENGTH: 35
<212> TYPE: DNA
<213> ORGANISM: Artificial
<220> FEATURE:
<223> OTHER INFORMATION: primer

<400> SEQUENCE: 41
caccatgtgt tttaataaca ttgaaactgg tgatg                            35

<210> SEQ ID NO 42
<211> LENGTH: 27
<212> TYPE: DNA
<213> ORGANISM: Artificial
<220> FEATURE:
<223> OTHER INFORMATION: primer

<400> SEQUENCE: 42
attgtcttca cttcctgatt tatgatc                                    27

<210> SEQ ID NO 43
<211> LENGTH: 24
<212> TYPE: DNA
<213> ORGANISM: Artificial
<220> FEATURE:
<223> OTHER INFORMATION: primer

<400> SEQUENCE: 43
caccatggat ttgaacggtg agtg                                       24

<210> SEQ ID NO 44
<211> LENGTH: 19
<212> TYPE: DNA
<213> ORGANISM: Artificial
<220> FEATURE:
<223> OTHER INFORMATION: primer

<400> SEQUENCE: 44
agttcccaaa gcatcatcc                                             19

<210> SEQ ID NO 45
<211> LENGTH: 34

```
<212> TYPE: DNA
<213> ORGANISM: Artificial
<220> FEATURE:
<223> OTHER INFORMATION: primer

<400> SEQUENCE: 45
agaagtcgac tctagatgac tagtagcgag gaag                    34

<210> SEQ ID NO 46
<211> LENGTH: 37
<212> TYPE: DNA
<213> ORGANISM: Artificial
<220> FEATURE:
<223> OTHER INFORMATION: primer

<400> SEQUENCE: 46
tcgagctcgg taccettact tgtcgtcatc gtctttg                 37
```

The invention claimed is:

1. A method for obtaining a transgenic long day plant, comprising:
   (a) transforming into a long day plant a fusion polynucleotide comprising
      (i) a first polynucleotide sequence that consists of the nucleotide sequence shown in SEQ ID NO:5 or a nucleotide sequence having 95% or higher sequence identity to the nucleotide sequence shown in SEQ ID NO: 5 and that encodes a protein having an activity of suppressing the transcription of the circadian clock-associated 1 (CCA1) gene or the late elongated hypocotyl (LHY) gene, and
      (ii) a second polynucleotide sequence comprising one or more transcription activation domain sequences that consist of the nucleotide sequence shown in SEQ ID NO:11 or a nucleotide sequence having 95% or higher sequence identity to the nucleotide sequence shown in SEQ ID NO: 11 and that encodes a protein having an activity of releasing the suppression of transcription of the circadian clock-associated 1 (CCA1) gene or the late elongated hypocotyl (LHY) gene upon fusion thereof to a PRR polynucleotide,
      wherein the first polynucleotide sequence and the second polynucleotide sequence are under the control of a promoter;
   (b) selecting the transformed plant for exhibiting increased biomass selected from the group consisting of increased number of buds at floral bud formation, increased leaf area, and increased cross sectional area of the flower stem, and for having increased environmental stress resistance selected from the group of increased high salt resistance, increased dehydration resistance, and increased low temperature stress resistance as compared to a wild type long day plant; and
   (c) thereby obtaining a transgenic long day plant.

* * * * *